US012586391B2

(12) United States Patent
Ho et al.

(10) Patent No.: US 12,586,391 B2
(45) Date of Patent: Mar. 24, 2026

(54) SYSTEMS AND METHODS FOR DECONVOLVING CELL TYPES IN HISTOLOGY SLIDE IMAGES, USING SUPER-RESOLUTION SPATIAL TRANSCRIPTOMICS DATA

(71) Applicant: TEMPUS AI, INC., Chicago, IL (US)

(72) Inventors: Chi-Sing Ho, Redwood City, CA (US); Tianyou Luo, Chapel Hill, NC (US); Ameen Salahudeen, Oak Park, IL (US); Luca Lonini, Chicago, IL (US)

(73) Assignee: TEMPUS AI, INC., Chicago, IL (US)

( * ) Notice: Subject to any disclaimer, the term of this patent is extended or adjusted under 35 U.S.C. 154(b) by 244 days.

(21) Appl. No.: 18/511,998

(22) Filed: Nov. 16, 2023

(65) Prior Publication Data

US 2024/0161519 A1 May 16, 2024

Related U.S. Application Data

(60) Provisional application No. 63/426,009, filed on Nov. 16, 2022.

(51) Int. Cl.
*G06V 20/69* (2022.01)
*G06T 3/40* (2024.01)
(Continued)

(52) U.S. Cl.
CPC .............. *G06V 20/698* (2022.01); *G06T 3/40* (2013.01); *G06T 7/0012* (2013.01); *G06T 7/10* (2017.01); *G06T 7/149* (2017.01); *G06V 10/46* (2022.01); *G06V 10/82* (2022.01); *G06V 20/695* (2022.01); *G16H 30/40* (2018.01); (Continued)

(58) Field of Classification Search
CPC ........... G06T 3/40; G06T 7/0012; G06T 7/10; G06T 7/149; G06T 2207/10056; G06T 2207/20081; G06T 2207/20084; G06T 2207/20132; G06T 2207/30024; G06V 10/44; G06V 10/46; G06V 10/70; G06V 10/764; G06V 10/82; G06V 20/69;
(Continued)

(56) References Cited

U.S. PATENT DOCUMENTS 10,957,041 B2    3/2021    Yip et al.
10,991,097 B2    4/2021    Yip et al.
(Continued)

OTHER PUBLICATIONS

Zhao et al. "Innovative super-resolution in spatial transcriptomics: a transformer model exploiting histology images and spatial gene expression." Briefings in Bioinformatics, 25(2), pp. 1-15 (Year: 2024).*
(Continued)

*Primary Examiner* — Scott A Rogers
(74) *Attorney, Agent, or Firm* — MARSHALL, GERSTEIN & BORUN LLP

(57) ABSTRACT

A computer-implemented method, computing system and computer-readable medium include receiving training data and training a machine learning model to generate a cell expression map. A computer-implemented method, computing system and computer-readable medium includes receiving a histology image and a cell segmentation map and processing them using a trained machine learning model.

22 Claims, 29 Drawing Sheets
(26 of 29 Drawing Sheet(s) Filed in Color)

(51) Int. Cl.

| | |
|---|---|
| *G06T 7/00* | (2017.01) |
| *G06T 7/10* | (2017.01) |
| *G06T 7/149* | (2017.01) |
| *G06V 10/46* | (2022.01) |
| *G06V 10/82* | (2022.01) |
| *G16H 30/40* | (2018.01) |

(52) U.S. Cl.
CPC .............. *G06T 2207/10056* (2013.01); *G06T 2207/20081* (2013.01); *G06T 2207/20132* (2013.01); *G06T 2207/30024* (2013.01)

(58) Field of Classification Search
CPC .. G06V 20/693; G06V 20/695; G06V 20/698; G16H 30/40
See application file for complete search history.

(56) References Cited

U.S. PATENT DOCUMENTS

| | | | |
|---|---|---|---|
| 11,348,239 B2 | 5/2022 | Yip et al. | |
| 2024/0266002 A1* | 8/2024 | Adeleke ................. | G16H 50/70 |
| 2025/0014681 A1* | 1/2025 | Zhang ................... | G06T 7/0012 |
| 2025/0218534 A1* | 7/2025 | Jaganathan ............ | G16B 25/10 |

OTHER PUBLICATIONS

Biancalani et al. "Deep learning and alignment of spatially resolved single-cell transcriptomes with Tangram." Nature methods, 18(11), pp. 1352-1362 (Year: 2021).*

Duan, et al. "Spatially resolved transcriptomics: advances and applications." Blood Science, 5(1), pp. 1-14 (Year: 2023).*

Fang et al. "Computational approaches and challenges in spatial transcriptomics." Genomics, proteomics & bioinformatics, 21(1), pp. 24-47 (Year: 2023).*

Li et al. "Emerging artificial intelligence applications in spatial transcriptomics analysis." Computational and Structural Biotechnology Journal, 20, pp. 2895-2908 (Year: 2022).*

Liu et al. "Analysis and visualization of spatial transcriptomic data." Frontiers in genetics, 12, p. 785290 (Year: 2022).*

Murchan et al. "Deep learning of histopathological features for the prediction of tumor molecular genetics." Diagnostics, 11(8), p. 1406 (Year: 2021).*

Pang et al. "Leveraging information in spatial transcriptomics to predict super-resolution gene expression from histology images in tumors." BioRxiv, pp. 2021-11 (Year: 2021).*

Zeng et al. "Statistical and machine learning methods for spatially resolved transcriptomics data analysis." Genome biology, 23(1), p. 83 (Year: 2022).*

Aran et al., Reference-based analysis of lung single-cell sequencing reveals a transitional profibrotic macrophage, Nat. Immunol., 20(2): 163-172 (Feb. 2019).

Aran et al., xCell: digitally portraying the tissue cellular heterogeneity landscape, Genome Biology, 18: 220 (2017).

Bergenstrahle et al. Super-resolved spatial transcriptomics by deep data fusion, Nat Biotechnol., 40(4):476-479 (Apr. 2022).

Beaubier et al., Integrated genomic profiling expands clinical options for patients with cancer, Nat Biotechnol. 37(11): 1351-1360 (Nov. 2019).

Goltsev et al., Deep Profiling of Mouse Splenic Architecture with CODEX Multiplexed Imaging, Cell 174(4): 968-981 (Aug. 2018).

* cited by examiner

Super-resolution

Histology image      ISC expression

Super-resolved
expression

Film Coverslip
Glass Coverslip
No Coverslip

Sample 1
Sample 2
Sample 3
Sample 4
Sample 5
Sample 6
Sample 7

Cell Segmentation Map

Pathologist Annotations

202

Pathologist Annotations

302

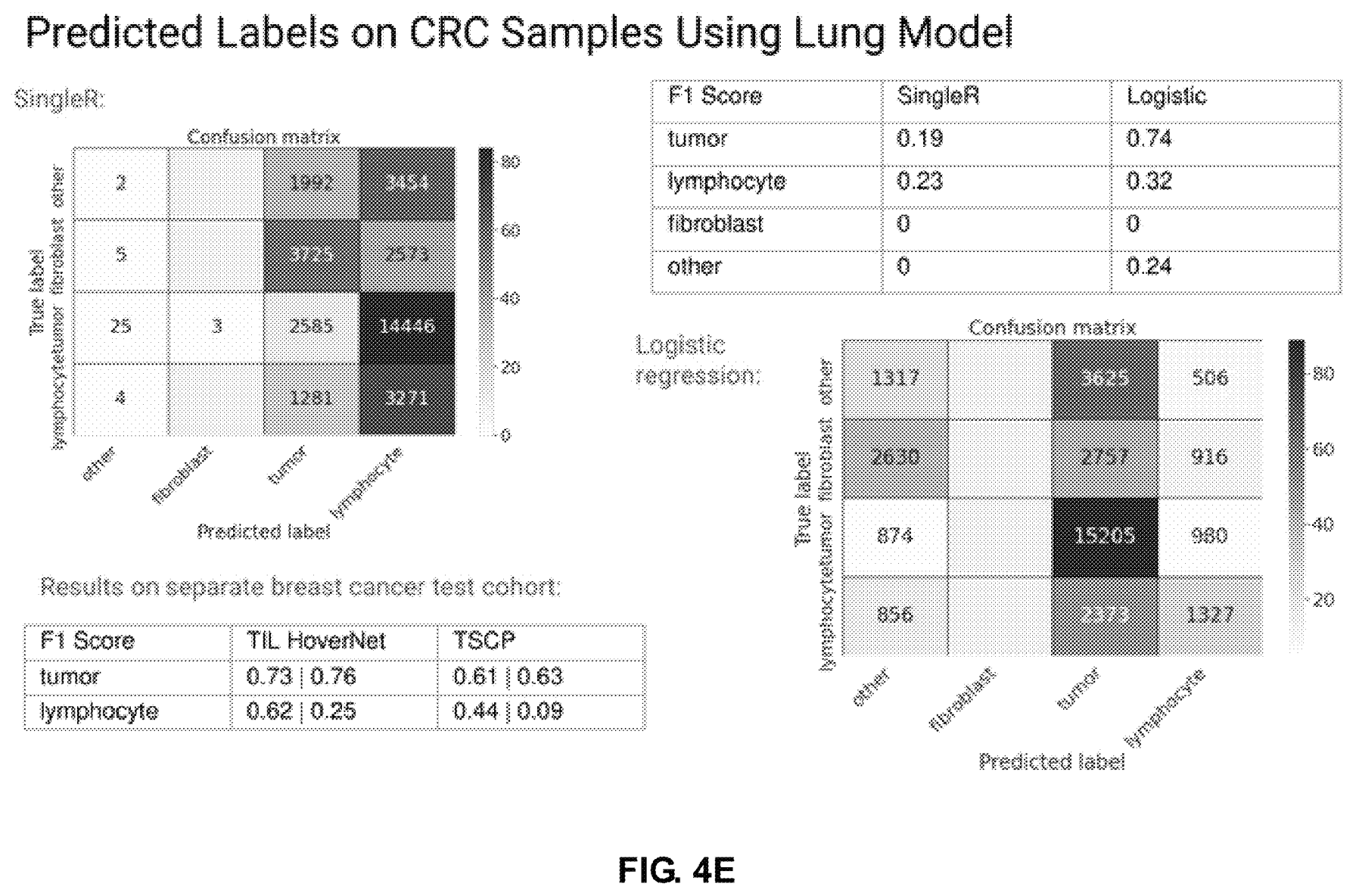

Predicted Labels on CRC Samples Using Lung Model

| F1 Score | SingleR | Logistic |
|---|---|---|
| tumor | 0.19 | 0.74 |
| lymphocyte | 0.23 | 0.32 |
| fibroblast | 0 | 0 |
| other | 0 | 0.24 |

Logistic regression:

Confusion matrix

|  | lymphocyte | tumor | fibroblast | other |
|---|---|---|---|---|
| lymphocyte | | | | 506 |
| tumor | | | | 916 |
| fibroblast | 15105 | | | 980 |
| other | | | | 1327 |
| | 1317 | | | |
| | | 4658 | | |
| | 874 | | | |
| | 856 | | | |

True label / Predicted label

SingleR:

Confusion matrix

| | lymphocyte | tumor | fibroblast | other |
|---|---|---|---|---|
| | 1947 | | 2 | |
| | 5779 | | 5 | |
| 14446 | 2585 | 3 | 25 | |
| 3971 | 1281 | | 4 | |

True label / Predicted label

Results on separate breast cancer test cohort:

| F1 Score | TIL HoverNet | TSCP |
|---|---|---|
| tumor | 0.73 \| 0.76 | 0.61 \| 0.63 |
| lymphocyte | 0.62 \| 0.25 | 0.44 \| 0.09 |

FIG. 4E

Predicted Labels on TiL BC Samples Using Lung Model

Logistic regression:

| F1 Score | SingleR | Logistic |
|---|---|---|
| tumor | 0.31 | 0.75 |
| lymphocyte | 0.16 | 0.01 |
| fibroblast | 0 | 0 |
| other | 0 | 0.02 |

Results on separate breast cancer test cohort:

| F1 Score | TiL HoverNet | TSCP |
|---|---|---|
| tumor | 0.73 \| 0.76 | 0.61 \| 0.63 |
| lymphocyte | 0.62 \| 0.25 | 0.44 \| 0.09 |

FIG. 4F

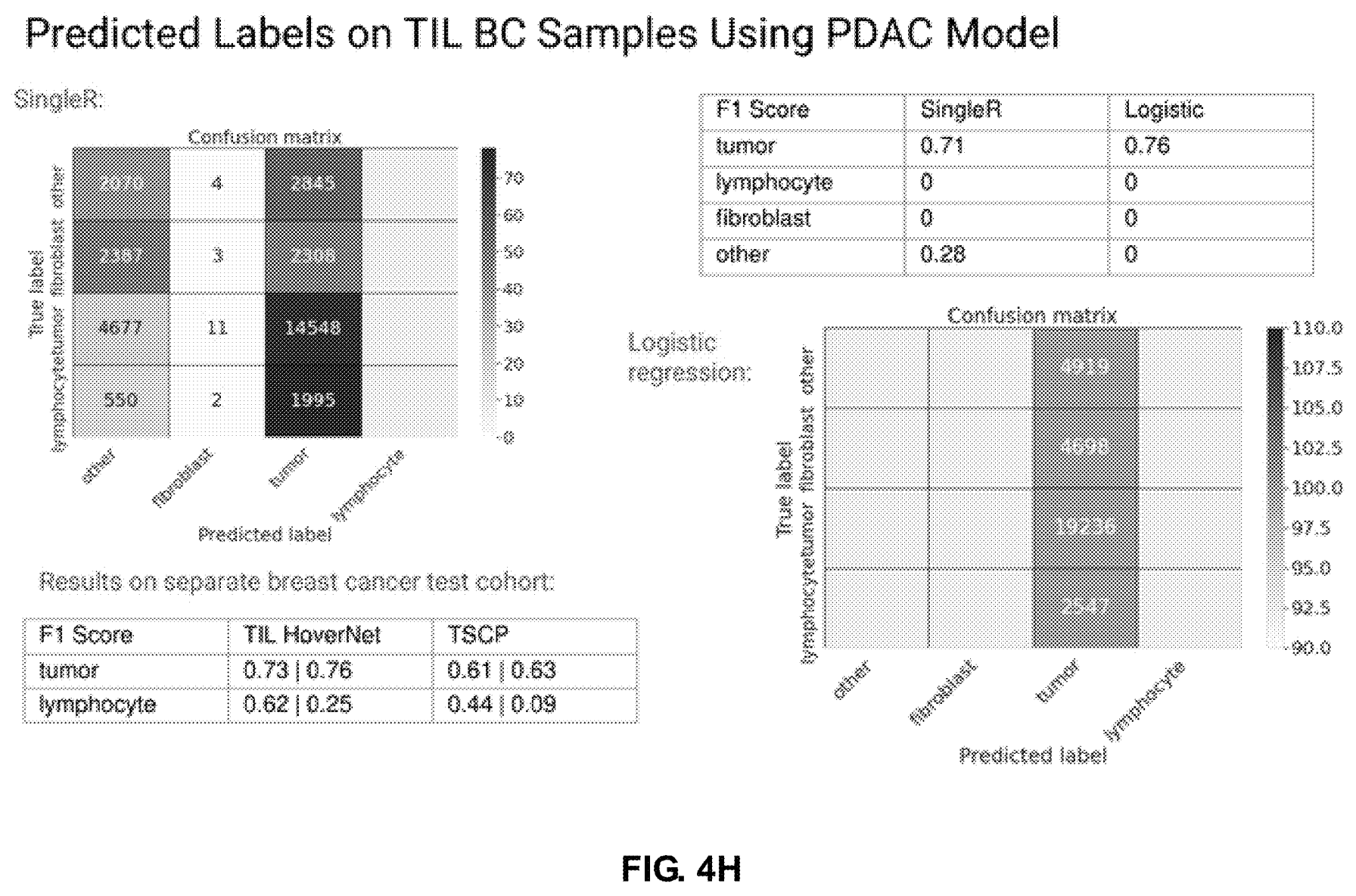

Predicted Labels on TIL BC Samples Using PDAC Model

SingleR:

| F1 Score | SingleR | Logistic |
|---|---|---|
| tumor | 0.71 | 0.76 |
| lymphocyte | 0 | 0 |
| fibroblast | 0 | 0 |
| other | 0.28 | 0 |

Logistic regression:

Results on separate breast cancer test cohort:

| F1 Score | TIL HoverNet | TSCP |
|---|---|---|
| tumor | 0.73 \| 0.76 | 0.61 \| 0.63 |
| lymphocyte | 0.62 \| 0.25 | 0.44 \| 0.09 |

FIG. 4H

Figure 4I:
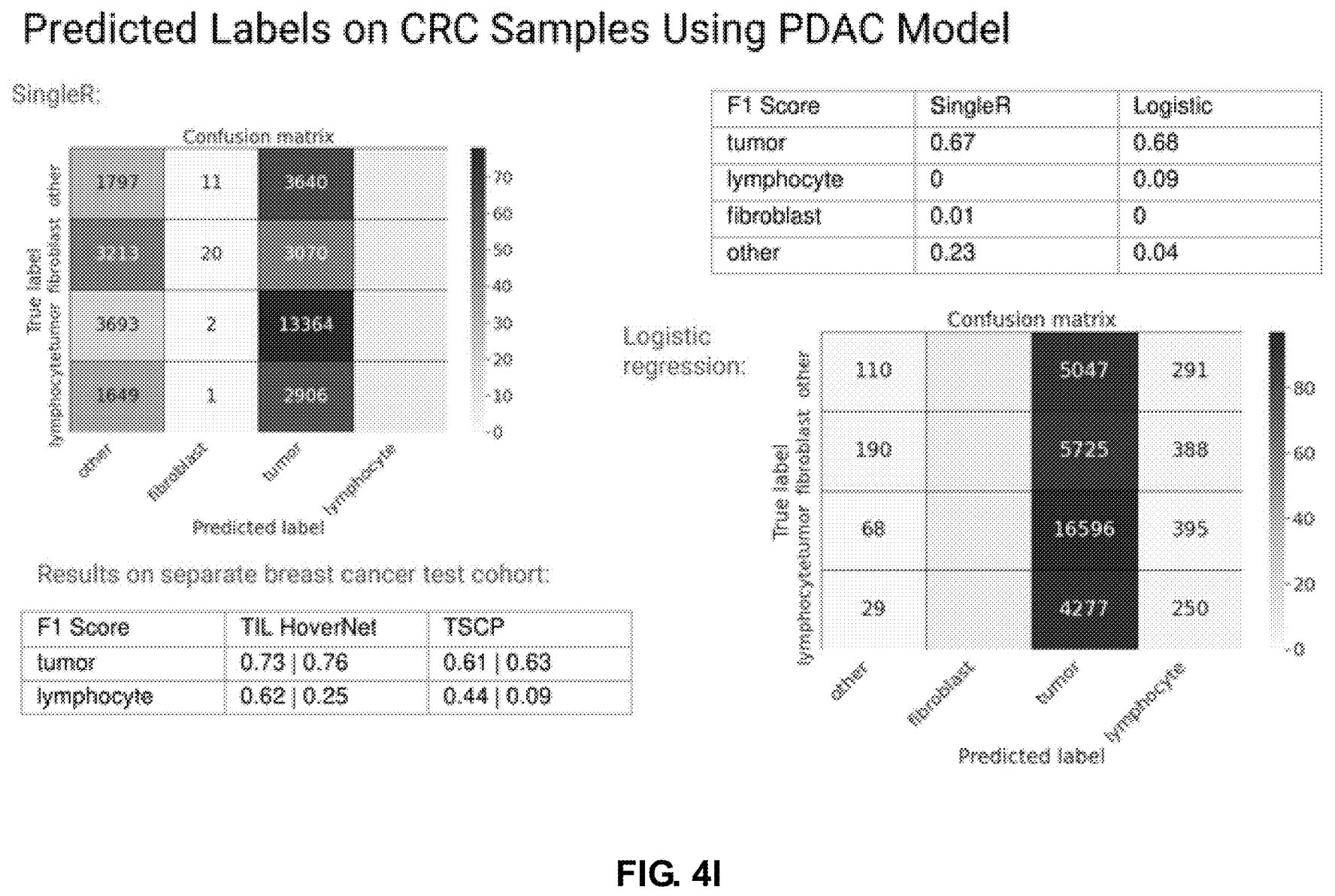

Predicted Labels on CRC Samples Using PDAC Model

| F1 Score | SingleR | Logistic |
|---|---|---|
| tumor | 0.67 | 0.68 |
| lymphocyte | 0 | 0.09 |
| fibroblast | 0.01 | 0 |
| other | 0.23 | 0.04 |

Logistic regression:

Confusion matrix

| | | | |
|---|---|---|---|
| 110 | 5047 | 291 | |
| 190 | 5725 | 388 | |
| 68 | 16596 | 395 | |
| 29 | 4277 | 250 | |

True label (lymphocyte tumor fibroblast other)

Predicted label (lymphocyte tumor fibroblast other)

SingleR:

Confusion matrix

Predicted label

True label (lymphocyte tumor fibroblast other)

Results on separate breast cancer test cohort:

| F1 Score | TIL HoverNet | TSCP |
|---|---|---|
| tumor | 0.73 \| 0.76 | 0.61 \| 0.63 |
| lymphocyte | 0.62 \| 0.25 | 0.44 \| 0.09 |

RECEIVE TRAINING DATA

604

TRAIN MACHINE LEARNING MODEL, USING TRAINING DATA, TO
GENERATE CELL EXPRESSION MAP CORRESPONDING TO
CROPPED PORTION OF SUPER-RESOLVED GENE EXPRESSION
HEAT MAP

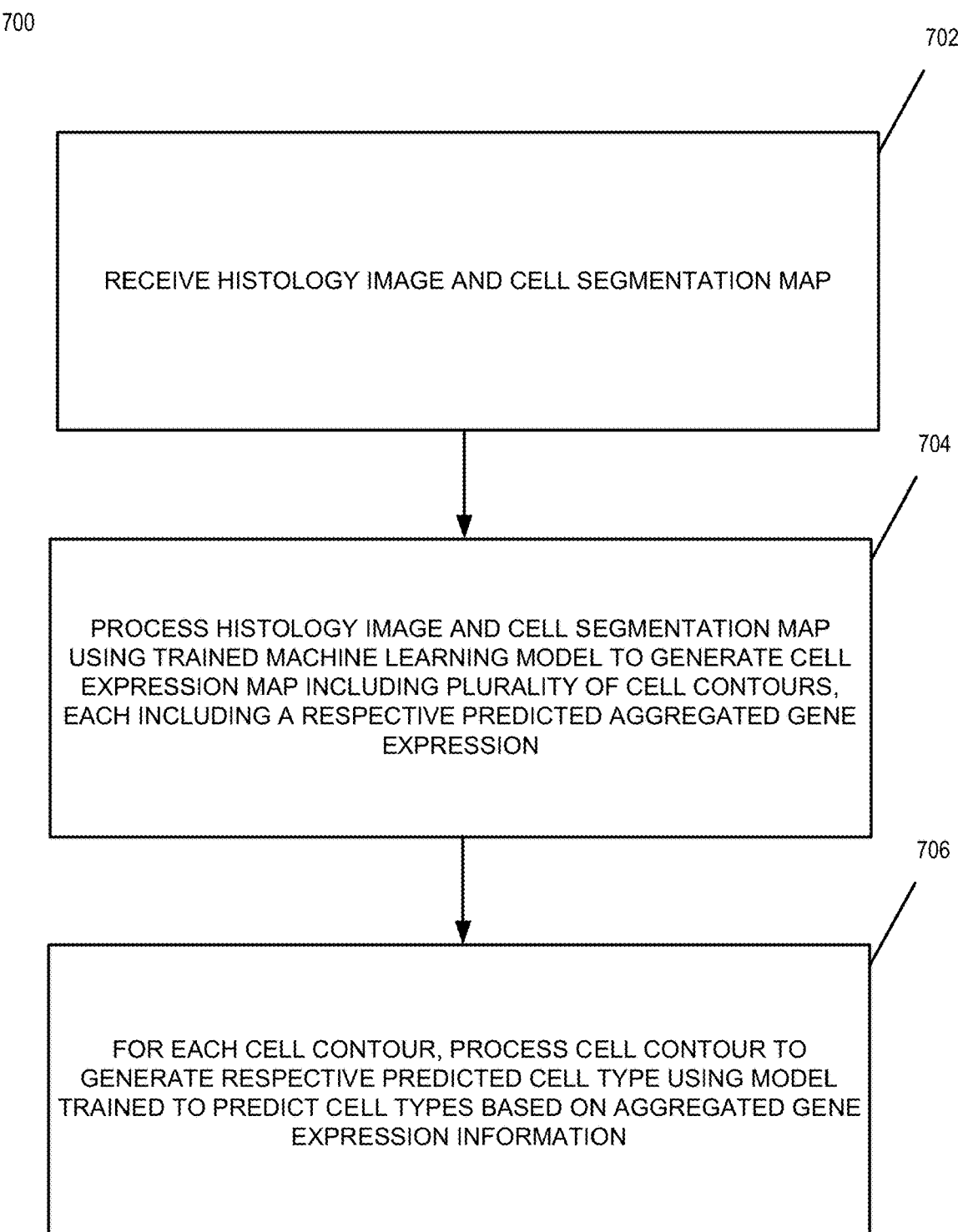

700

702

RECEIVE HISTOLOGY IMAGE AND CELL SEGMENTATION MAP

704

PROCESS HISTOLOGY IMAGE AND CELL SEGMENTATION MAP USING TRAINED MACHINE LEARNING MODEL TO GENERATE CELL EXPRESSION MAP INCLUDING PLURALITY OF CELL CONTOURS, EACH INCLUDING A RESPECTIVE PREDICTED AGGREGATED GENE EXPRESSION

706

FOR EACH CELL CONTOUR, PROCESS CELL CONTOUR TO GENERATE RESPECTIVE PREDICTED CELL TYPE USING MODEL TRAINED TO PREDICT CELL TYPES BASED ON AGGREGATED GENE EXPRESSION INFORMATION

FIG. 7

SYSTEMS AND METHODS FOR DECONVOLVING CELL TYPES IN HISTOLOGY SLIDE IMAGES, USING SUPER-RESOLUTION SPATIAL TRANSCRIPTOMICS DATA

CROSS-REFERENCE TO RELATED APPLICATIONS

The present application claims priority to U.S. Provisional Application No. 63/426,009, entitled SYSTEMS AND METHODS FOR DECONVOLVING CELL TYPES IN HISTOLOGY SLIDE IMAGES, USING SUPER-RESOLUTION SPATIAL TRANSCRIPTOMICS DATA, filed on Nov. 16, 2022, and hereby incorporated by reference in its entirety.

FIELD OF THE INVENTION

The present disclosure is directed to improvements related to methods and systems for using spatial transcriptomics data to assign cell types to cells/deconvolve cells on pathology slides.

BACKGROUND

Next-generation sequencing of bulk cell populations has become a useful and ubiquitous tool for the molecular characterization of clinical tumor samples. In general, bulk next-generation sequencing reveals transcript abundance within a tumor sample and can further infer cell populations via deconvolution algorithms (see, e.g., Beaubier N, Bontrager M, Huether R, Igartua C, Lau D, Tell R, Bobe A M, Bush S, Chang A L, Hoskinson D C, Khan A A, Kudalkar E, Leibowitz B D, Lozachmeur A, Michuda J, Parsons J, Perera J F, Salahudeen A, Shah K P, Taxter T, Zhu W, White K P. Integrated genomic profiling expands clinical options for patients with cancer. Nat Biotechnol. 2019 November; 37(11):1351-1360. doi: 10.1038/s41587-019-0259-z. Epub 2019 Sep. 30. PMID: 31570899). However, next-generation sequencing cannot ascribe the cellular context for a given gene's expression or elucidate the spatial organization of tumor microenvironments. And yet, these additional features can improve understanding of tumor biology and the development of immuno-oncology therapeutics.

Spatial transcriptomics (ST) is an emerging field that characterizes gene expression within the spatial context of tissue. ST data can be generated directly from archival formalin fixed paraffin embedded (FFPE) samples, enabling the study of spatial gene expression in real-world clinical settings. ST aims to bring the single cell resolution of conventional droplet-based single cell RNA-seq to intact FFPE tissue sections.

There is interest in identifying novel targets with greater resolution and clarity around binding sites. As bulk RNA-seq data has become ubiquitous, the inability to resolve targets in distinct cell populations has remained a major challenge. Given the inherent difficulties with sample requirements for droplet-based single cell RNA-seq, and lack of spatial context, single cell RNA-seq based insights have not become a standard data element in drug development and translational research. Because ST is compatible with standard FFPE tissue and enables transcriptomic reads to be obtained directly from standard stained hematoxylin and eosin (H&E) tissue slides, ST enables true cell-level labeling with spatial context. Thus, there is interest in using ST to facilitate novel target discovery, prediction of response to novel immunotherapies, and trial design. Furthermore, despite advances in spatial transcriptomic resolution to subcellular spots (i.e., <5-10 micron), there remains the problem of registering transcriptomic data to the correct cells in the case of multiple cells overlapping the same spot which arises from difficulties with automated cell segmentation algorithms.

Spatial transcriptomics using current ST technologies has the ability to provide spatially-resolved transcriptomic data on fixed tissue samples. However, the spatial resolution of such data is still low (e.g., 10-100 cells per spot), and does not provide cell type classifications within each spot. Conventional techniques that seek to improve the resolution of current ST technologies have not been fully developed or validated for cell classification. In particular, such conventional techniques attempt to produce super-resolved gene maps but do not provide a model for classifying cells from super-resolved gene maps. Further, such conventional techniques may transform ST data (RNA expression levels for each spot on a slide, where one spot could have 10-100 cells) into high resolution data where each pixel has associated RNA expression levels for each gene, and there are multiple pixels within each cell. However, each pixel does not correlate to a single cell. Furthermore, the validation attempted by such conventional techniques includes simulated synthetic expression maps, dropping certain spots and performing imputation (using the same slide), validating prediction on held-out human squamous cell carcinoma slide (with same tissue sample, or a serial tissue section) and testing of model sensitivity and robustness by introducing distortion to the H&E images. These techniques may withhold from the model during training. Accordingly, there is an opportunity for platforms and technologies that provide improved pathology slide image cell classification based on spatial transcriptomics data.

SUMMARY OF THE INVENTION

In an aspect, a computer-implemented method for training a machine learning model to classify cells in a histology image includes (i) receiving, via one or more processors, training data; and (ii) training a machine learning model, using the training data, to generate a cell expression map corresponding to a cropped portion of a super-resolved gene expression heat map, wherein the cell expression map includes a plurality of cell contours, each including respective aggregated gene expression values.

In another aspect, a computer-implemented method for classifying cells in an histology image includes (i) receiving, via one or more processors, the histology image and a cell segmentation map; (ii) processing the histology image and the cell segmentation map using a trained machine learning model to generate a cell expression map including a plurality of cell contours, each including a respective predicted aggregated gene expression, wherein the machine learning model is trained using training data; and (iii) for each of the cell contours, processing the cell contour to generate a respective predicted cell type using a model trained to predict cell types based on aggregated gene expression information.

In yet another aspect, a computing system for training a machine learning model to classify cells in a histology image includes one or more processors; and one or more memories having stored thereon computer-executable instructions that, when executed by the one or more processors, cause the computing system to: (i) receive, via one or more processors, training data; and (ii) train a machine learning model, using the training data, to generate a cell expression map corresponding to a cropped portion of a super-resolved gene expression heat map, wherein the cell expression map includes a plurality of cell contours, each including respective aggregated gene expression values.

In yet another aspect, a computing system for training a machine learning model to classify cells in a histology image includes one or more processors; and one or more memories having stored thereon computer-executable instructions that, when executed by the one or more processors, cause the computing system to: (i) receive, via one or more processors, the histology image and a cell segmentation map; (ii) process the histology image and the cell segmentation map using a trained machine learning model to generate a cell expression map including a plurality of cell contours, each including a respective predicted aggregated gene expression, wherein the machine learning model is trained using training data; and (iii) for each of the cell contours, process the cell contour to generate a respective predicted cell type using a model trained to predict cell types based on aggregated gene expression information.

In still another aspect, a non-transitory computer-readable medium includes computer-executable instructions that, when executed by one or more processors, cause a computer to: (i) receive, via one or more processors, training data; and (ii) train a machine learning model, using the training data, to generate a cell expression map corresponding to a cropped portion of a super-resolved gene expression heat map, wherein the cell expression map includes a plurality of cell contours, each including respective aggregated gene expression values.

In yet another aspect, a non-transitory computer-readable medium includes computer-executable instructions that, when executed by one or more processors, cause a computer to: (i) receive, via one or more processors, the histology image and a cell segmentation map; (ii) process the histology image and the cell segmentation map using a trained machine learning model to generate a cell expression map including a plurality of cell contours, each including a respective predicted aggregated gene expression, wherein the machine learning model is trained using training data; and (iii) for each of the cell contours, process the cell contour to generate a respective predicted cell type using a model trained to predict cell types based on aggregated gene expression information.

BRIEF DESCRIPTION OF DRAWINGS

This patent or application file contains at least one drawing executed in color. Copies of this patent or patent application publication with color drawing(s) will be provided by the United States Patent and Trademark Office upon request and payment of the necessary fee.

FIG. 4E depicts a confusion matrix for the SingleR prediction and logistic regression.

FIG. 4F depicts a confusion matrix for the SingleR prediction and logistic regression.

FIG. 4H depicts a confusion matrix for the TIL BC samples/PDAC model.

FIG. 4I depicts a confusion matrix for the CRC samples/PDAC model discussed above.

FIG. 7 depicts an exemplary method, according to some aspects.

Figure 1A:
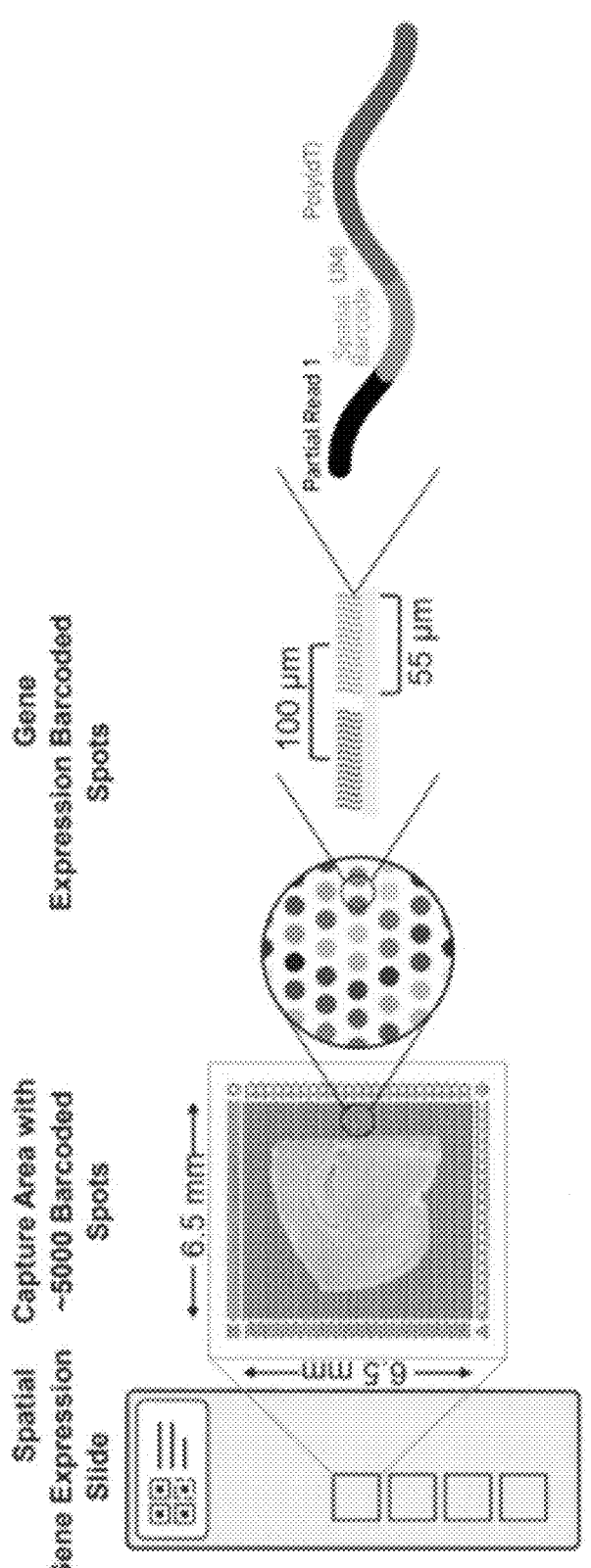
FIG. 1A depicts a prior art spatial transcriptomics technology.

The figures described below depict various aspects of the system and methods disclosed herein. It should be understood that each figure depicts an example of aspects of the present systems and methods.

DETAILED DESCRIPTION

Overview

The present techniques are directed to, inter alia, validation of super-resolution of spatial transcriptomics (ST) data, and more particularly, to the development of custom models capable of deconvolving cellular populations within formalin fixed paraffin embedded (FFPE) slides from H&E hematoxylin and eosin (H&E) tissue slides. In some aspects, the present techniques may include a custom model that processes super-resolved transcriptomics data (for example, outputs of a low-to-high resolution ST model) and computes cell type classifications to deconvolve the cellular populations within a FFPE slide from an H&E image. The aforementioned low-to-high resolution ST model may be any model trained to receive low resolution ST data (e.g., ST data having more than one biological cell associated with each gene expression value) and transform the low resolution ST data into high resolution ST data (e.g., ST data having between zero to one biological cells associated with each gene expression value). In some aspects, the transformation may be based on the image of a histology slide tissue slice associated with the ST data.

In some aspects, the low-to-high resolution ST model may be run on a cohort of annotated slides to generate high resolution gene maps for genes selected by one or more users (e.g., one or more scientists). Instead of prior art slides limited to one expression level per gene per spot/10-100 cells, the slides of the present techniques may have one expression level per gene in each pixel, wherein each biological cell encompasses at least one pixel, usually multiple pixels).

The present techniques may further include generating nucleus segmentations using a slide classification pipeline (SCP), and deriving cell type classifications from these high resolution gene maps by training a classification model on pathologist cell annotations. In some aspects, cell types may include tumor and immune cell types (e.g., lymphocytes, macrophages, fibroblasts, etc.). In some aspects, the SCP may generate a cell mask that is applied to the low-to-high resolution ST model image/heat map for each selected gene. In some aspects, all pixels for one gene may be aggregated within each cell to create a single gene expression level for the cell, for that gene). In some aspects, the selected genes may include immune cell markers. It is envisioned that selected genes may also include cancer cell markers. The result of the SCP may be a gene expression profile for a cell that a gene expression level for each of the selected genes.

In some examples, identifying cells within digital images using a trained cell segmentation model comprises applying, using the one or more processors, each of the images to the cell segmentation model and, for each image, assigning a cell classification to one or more pixels within the tile image. In some examples, assigning the cell classification to one or more pixels within the image comprises identifying, using the one or more processors, the one or more pixels as a cell interior, a cell border, or a cell exterior and classifying the one or more pixels as the cell interior, the cell border, or the cell exterior. In some examples, the trained cell segmentation model is a pixel-resolution three-dimensional UNet classification model trained to classify a cell interior, a cell border, and a cell exterior.

The present techniques may include analyzing each cell's gene expression profile using a trained machine learning model (e.g., a trained logistic regression model) to determine a type of the cell. In some aspects, the trained machine learning model may be trained using pathologist-annotated slides with paired gene expression profiles for the cells, generated, for example, by applying segmented cell masks to ST data transformed by the low-to-high resolution ST model. In some aspects, the logistic regression model may be trained by single cell seq data from known, purified cell types. For example, the output of the machine learning model may be one or more spatially-resolved cell classification output per H&E slide. In some aspects, the present techniques may include inference of perturbed human explant model systems of drugs acting on immune cells, stromal cells or all cell populations in the context of a native tissue sample. The present techniques may include other techniques, now known or future developed, that provide similar modeling environments. Additional hardware, instrumentation, devices, laboratory equipment and/or sampling methodologies may be added to FIG. 5 to facilitate such designs.

It will be appreciated by those of ordinary skill in the art that the present techniques may be used to license cell deconvolution data to pharmacy industry clients for FDA approved, in clinical or pre-clinical development. There are currently few model systems to evaluate human immunology drugs and the systems are low quality. The present technique may also be used to provide reliable ground truth training data to algorithms that receive spatial transcriptomics, and/or histology slide images having labeled cell types during training. The present techniques may be used to allow for high resolution interpretation of heterotypic cell: cell interactions which underlies disease pathophysiology and disrupting or enhancing the cell:cell interactions may be exploitable for therapeutic purposes.

The data generated by the present techniques are of interest to clinical testing as a means to provide quality assurance and to AI algorithm development because the data future-proof R&D spend on data sets (e.g. training models on serial sections with IHC and H&E, which is limited to one protein at a time and yields only region-level, not cell-level labels). On the other hand, ST yields the entire transcriptome to train on with the potential to generate cell-level labels. Further, ST can increase the success of matching patients to clinical trials for novel immunotherapies by identifying eligible cohorts. Still further, ST advantageously enables/unlocks downstream algorithm development via large-scale labeled datasets, allows for TIL quantification and can improve biomarker detection in bulk RNA of samples with low tumor purity. The present techniques are applicable both to low resolution ST (e.g., from relatively large areas of tissue), intermediate resolution (greater resolution but not cell-level) and to high resolution (e.g., single-cell level). The present techniques appropriately assign transcriptomic data to the correct cells in cases where high resolution data may already exist.

Deidentified data generated by the systems and methods disclosed herein can be utilized by various research and/or industrial entities, either without or paired with de-identified clinical and molecular data. For example, these systems and methods could be used to analyze patient histology slides to determine whether the patient has a particular target or cell population that indicates the patient would be successfully treated by a particular therapy, for example a biologic (e.g. monoclonal antibody) targeting a specific target and cell population. This technology could be used for bulk RNA cell type deconvolution from ST. In various embodiments, this technology could be used instead of droplet based scRNA-seq and/or CITE-seq. For example, the present techniques are applicable to certain types of cancer therapy tools, such as Chimeric Antigen Receptor cells or bispecific antibodies, both of which require a distinction between tumor cell expression of target tissue, on one hand, and immune or normal/parenchyma tissue on the other.

The present techniques are useful for drug discovery and development: In addition to spatially deconvolving RNAseq data to better understand tumor biology and microenvironments, ST advantageously eliminates a tedious and time consuming step of mapping candidate drug targets to tumor cells via IHC or other staining modalities. This is especially true for drug development of biologics (e.g., mAbs and ADCs), the latter being a high priority in the wake of success with immuno oncology therapies. Having these data at scale in a well-structured database similar to a bulk RNA-seq will be highly valued by the pharma industry.

In general, the present techniques demonstrate the feasibility and robustness of spatial transcriptomics to investigate spatial gene expression signatures in retrospective clinical cohorts. Specifically, by demonstrating that clinical archival FFPE samples yield high interassay reliability (e.g., via the CytAssist platform). This improves precision oncology by enabling deeper understandings of cellular context to empower discovery and translational efforts.

As noted above, ST aims to bring the single cell resolution of conventional droplet-based single cell RNA-seq to intact FFPE tissue sections. Drug targets are also of interest in spatially localized interfaces between cell populations. For example, PD-1/PD-L1 interfaces between exhausted T lymphocytes and PD-L1 expressing tumor cells for immune checkpoint blockade. Similar immune-tumor cell interactions or other heterotypic cellular interactions are potential avenues for therapeutics development.

Exemplary Spatial Transcriptomics Techniques

In general, ST is needed because location matters for gene expression values. Before ST, single cell RNA seq/sc-seq or bulk RNA seq reactions would mix up the cells, and the data could not provide information about the cellular micro environment (spatial relationship between each pair of cells in the sample). ST has enabled investigation of gene expression in the context of spatial organization, without the need to break tissue first.

FIG. 1A depicts exemplary prior art spatial transcriptomics (ST) technologies. In general, conventional ST platforms are systems for generating sequencing transcriptomics data from histology slides, which may comprise a surface having capture probes, wherein the surface can capture nucleic acids from permeabilized cells on a histology slide by coming into contact with the histology slide and wherein the capture probes in a particular location on the surface have a sequence barcode unique to that location, such that a sequence read can be matched to the location based on the sequence barcode. Each barcoded location may be arranged in a grid.

Existing spatial gene expression/molecular profiling solutions may be able to classify tissue based on total mRNA and, in some instance, map the whole transcriptome with morphological context in FFPE or fresh frozen tissues to discover insights into normal development, disease pathology, and clinical translational research. Such profiling solutions may provide an ST slide with many (e.g., 10,000 or more barcoded spots). A barcode may be attached to partial reads, to demonstrate where each read in resulting data comes from with spatial context, as shown in FIG. 1A. Benefits of ST include avoiding tissue dissociation, retaining organization of tissue and cellular microenvironment; and bridging expression data with H&E images.

Figure 1B:
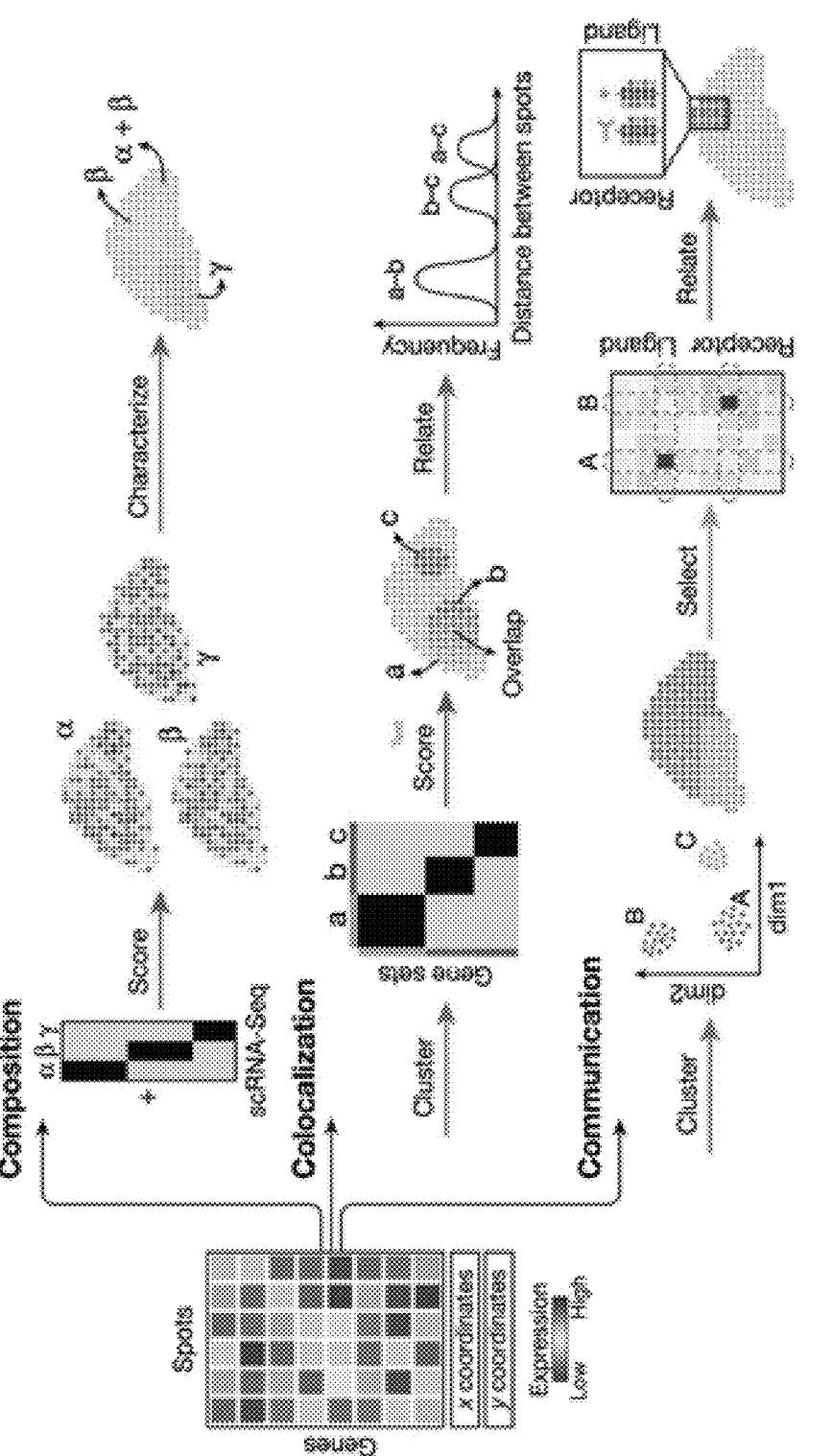
FIG. 1B depicts prior art operational paths for analysis of a gene expression matrix generated using spatial transcriptomics technology.

FIG. 1B depicts prior art operational paths for analysis of a gene expression matrix generated using ST technology. ST can be used for research purposes including cell type composition, cell co-localization, and cell-cell interaction, as depicted in FIG. 2B.

Figure 1C:
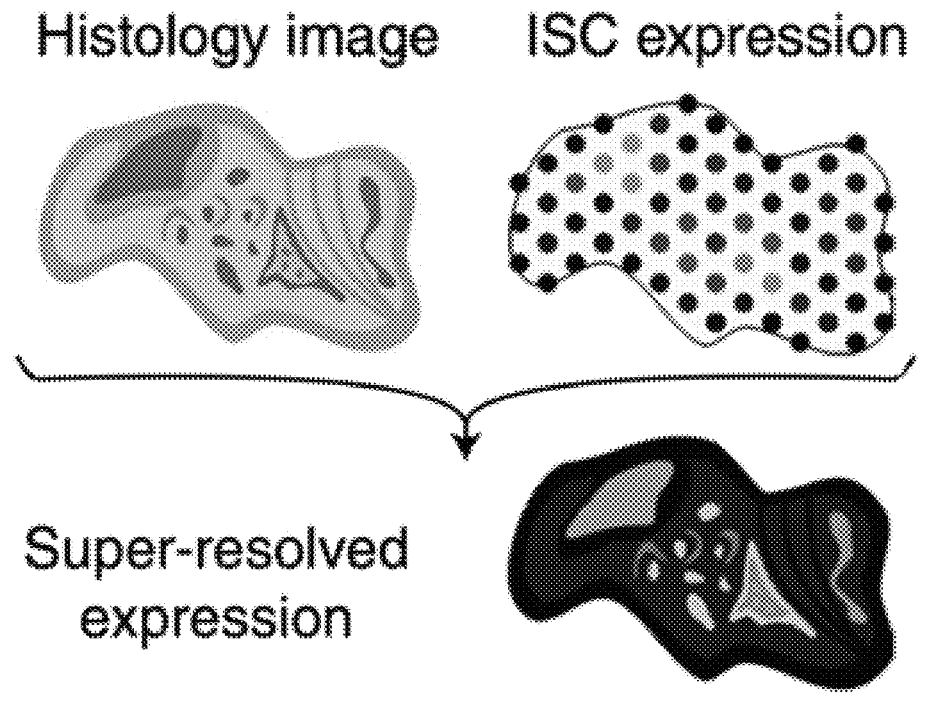
FIG. 1C depicts an overview of a low-to-high resolution ST model super resolution technique.

FIG. 1C depicts an overview of the low-to-high resolution ST model super resolution technique. As discussed above, despite the advantages of ST, there are still some technical limitations to conventional ST platforms.

For example, these platforms cannot reach single cell resolution, unlike sc-seq. The spatial gene expression map on a spot (resolution) level, consists of about 10-100 cells. Scientists have a rough understanding of what the spatial gene expression looks like, but details are lacking. The low-to-high resolution ST model was developed to perform super resolution based on histology imaging and spot level transcription data, to obtain a more finer details about the spatial gene expressions. The basic idea of the low-to-high resolution ST model is to use data from the image side to help enhance the resolution on the gene expression side of ST data, as shown in FIG. 1C.

However, the model of the low-to-high resolution ST model trained on ST experiments does nothing to address a world of unexplored histology images that do not have accompanying gene expression/ST data. The present techniques are motivated by a recognition that there may value in obtaining predictive expressions from a trained machine learning model.

Figure 1D:
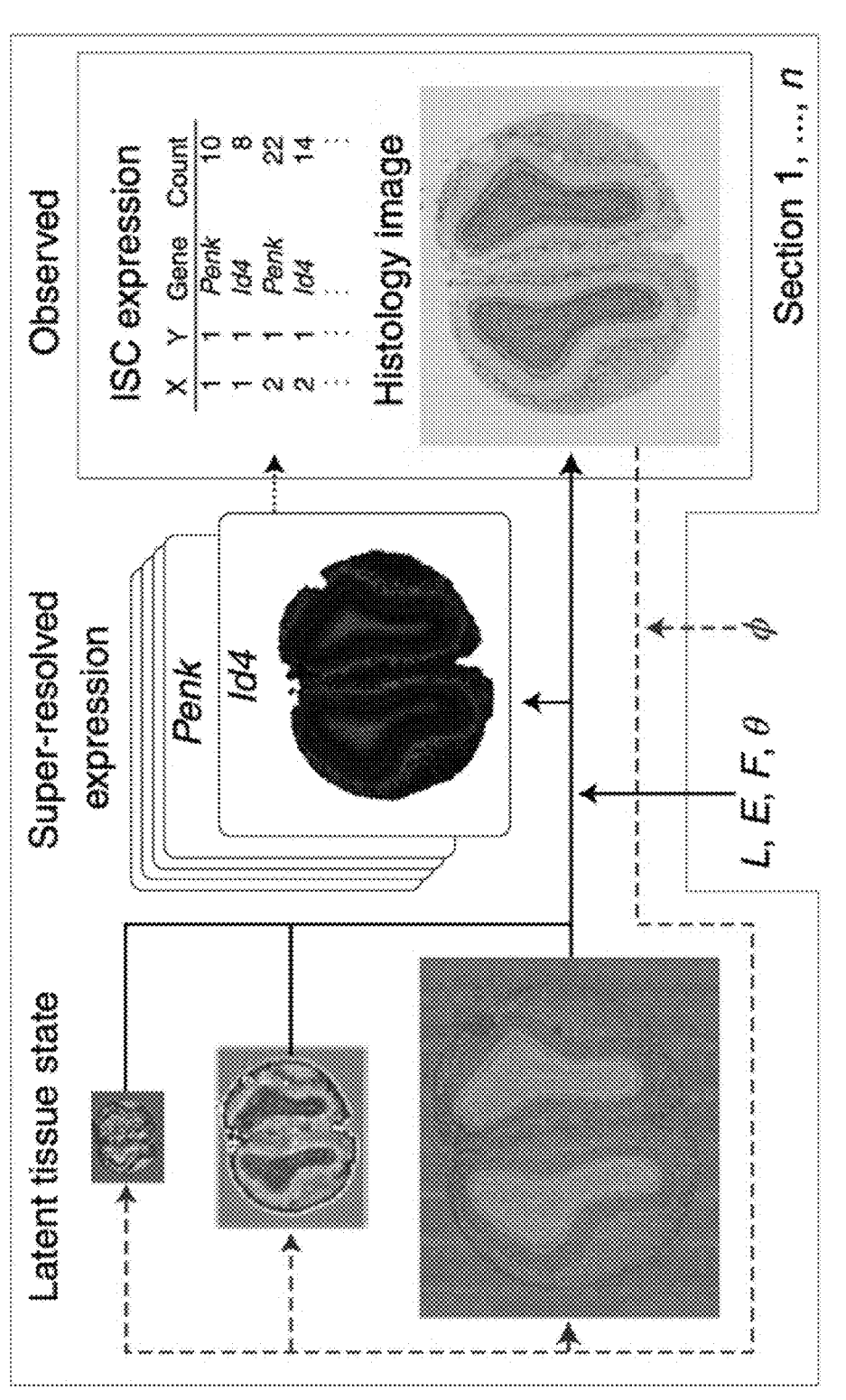
FIG. 1D depicts an exemplary low-to-high resolution ST model training flow diagram.

FIG. 1D depicts an exemplary the low-to-high resolution ST model training flow diagram. The model may receive observed high resolution histology images and ST data and may output a gene expression map for each gene at the same pixel resolution as the input high resolution histology image. During a training phase, the gene expression labels at low spot level resolution may be used to guide the training through the loss functions. The model structure itself may be structured similar to a generational encoder. AN underlying assumption that there is a latent tissue state of each image that represents encoded features, wherein gene expression values are assumed to be generated based on the latent tissue states of each image. Latent tissue state may be modeled at different resolutions.

From this multi resolution tissue state to the gene expression values, they further assumed this process was mediated by some meta genes in between. Which physically is a group representation of all the genes used in the model. From the metagene activity or expressions generated from the latent tissue states, the innovative gene values are generated by giving different weights to those metagenes. The model training may include classical modeling assumptions for gene expression data, such as (negative/selective) binomial distributions to model final count values. The low resolution spot level gene expression labels may be matched with the pixel level just by adding together the corresponding spots' areas.

Figure 1E:
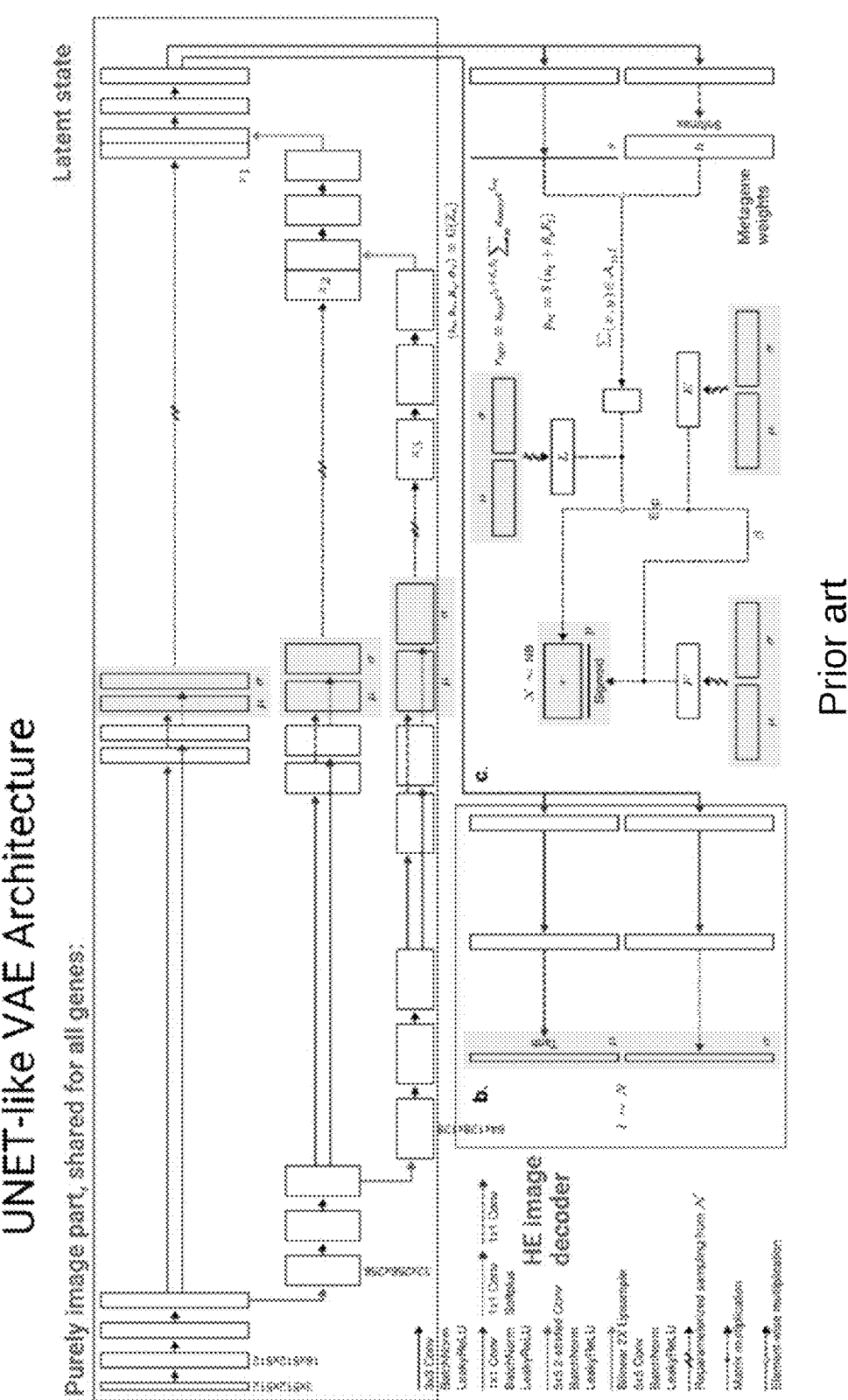
FIG. 1E depicts a detailed structural diagram of the low-to-high resolution ST model.

FIG. 1E depicts a detailed structural diagram of the low-to-high resolution ST model, which resembles U-net encoder. For example, an upper half of the low-to-high resolution ST model resembles U-net part, wherein the input is the histology image. The model may extract this latent tissue states in different resolutions. At the end, the Z here (upper right corner) is the latent tissue state that is modeled. Two decoders are used. The first is on the left side of the diagram, an H&E image decoder that takes the latent tissue state to try to reconstruct the H&E image.

Figure 1F:
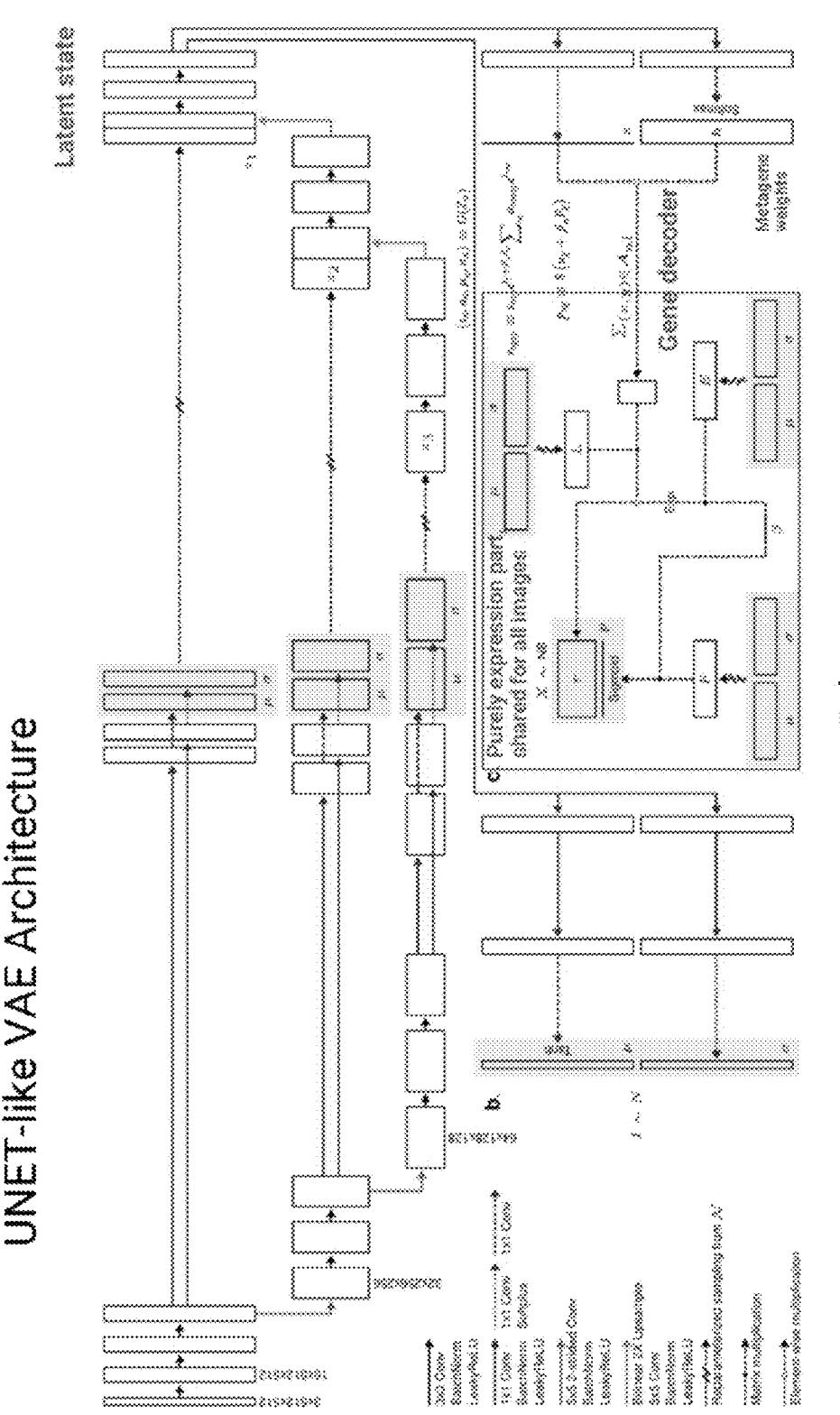
FIG. 1F depicts the second decoder of the low-to-high resolution ST model, according to some aspects.

FIG. 1F depicts the second decoder of the low-to-high resolution ST model, a gene expression decoder where the latent tissue state is used as input to generate metagene activities and weights of the metagenes and finally the gene expressions (pure expression parts shared between images). Advantages of the Present Validation and Prediction of Low-to-High Resolution ST Model Super-Resolution Techniques As discussed, the present techniques were the result of a recognition that ST techniques can also be used for refined cell type labeling and detailed investigation of tumor microenvironments, and that the low-to-high resolution ST model can be improved. Further, as discussed above, the validations included in the low-to-high resolution ST model were severely lacking. Specifically, the conventional validations primarily used the same slides or serial sections/ neighboring sections. These conventional validations did not cross-apply the trained model to slides from different tissue samples, or different cancer types. Further, the low-to-high resolution ST model did not aggregate pixel-wise results to the cell level, e.g. based on pixel-wise gene expression maps.

The present techniques improve the ability to explore how expression levels look from an individual cell resolution, and are based on pixel-wise gene expression maps, which are highly useful for analytical purposes. For example, from a research perspective, with a spatial map, an analyst can advantageously quickly and easily determine not only sub-type compositions of bulk tissue, but also the subtype composition of each spot for a small spatial neighborhood. With that information the relationship between cell types and how they interact with each other can also be explored.

By combining ST with H&E images and a spatial transcriptome map, the present techniques advantageously enable refined cell type labeling beyond labeling just based on cell type images, and a more detailed investigation of a tumor microenvironment, including how the tumor cells and immune cells interact with each other in tumor tissues. The present techniques further improve the purity of tumor tissue, by separating tumor boundaries from neighboring normal samples.

Validation Example 1

Figure 1G:
FIG. 1G depicts multiple FFPE tissue sections from patients in a proprietary database, sampled using different preparation conditions, according to some aspects of the present techniques.

In one aspect, a study included a dataset comprising six samples from non-small cell lung cancer patients and one core needle biopsy from a tumor of unknown origin. The study included using a sequencing platform to generate ST data and additionally generated paired bulk RNAseq data. To test the interassay reliability of the sequencing platform on archival FFPE tissue sections, the study compared ST results across three sample preparation conditions, as shown in FIG. 1G. For example, to test interassay reliability of CytAssist on archival FFPE tissue sections, FFPE tissue sections from 6 NSCLC and 1 tumor of unknown origin (TUO) samples may be selected from patients in a proprietary database. NSCLC samples may be collected via surgical resection (n=5) and fluid aspirate (n=1), and the TUO sample was collected as a core needle biopsy. In preparations 1 and 2, for example, Mayer's Hematoxylin may be manually applied, while in preparation 3, an autostainer with standard H&E reagents used. Additionally, paired bulk RNAseq libraries may be prepared from each FFPE sample, and multiplex immunofluorescence (IF) slides prepared from 2 of the NSCLC samples.

The study further investigated the state of the tumor microenvironment by applying state-of-the-art computational approaches to deconvolve immune cell populations and produce super-resolution ST maps, validated using multiplex immunofluorescence (IF) via CODEX (see xCell). In some aspects, the present techniques include analyzing the tumor microenvironment by estimating the abundance of immune cell populations using deconvolution of RNAseq data, and by applying xFuse (Bergenstråhle et al., 2022) to the ST data to produce super-resolution maps, validated using multiplex IF via CODEX (Goltsev et al., 2018).

Figure 1H:
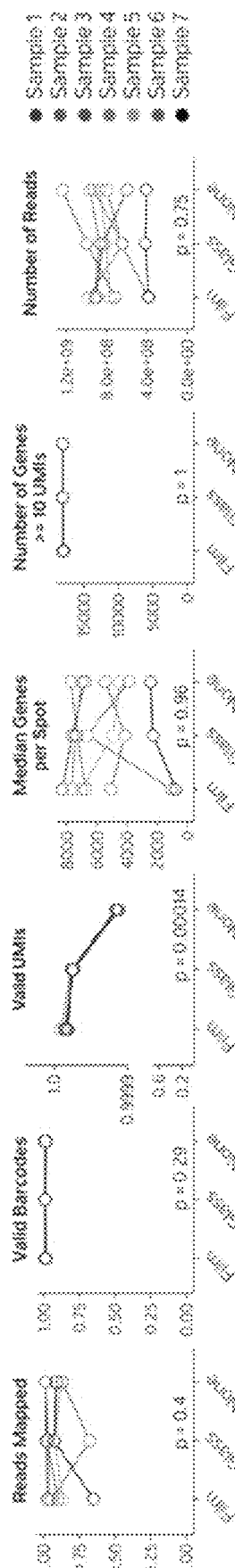
FIG. 1H depicts plots depicting Visium quality control metrics that are consistent across sample preparations, wherein P-values represent results of Kruskal-Wallis tests.
Figure 1I:
FIG. 1I depicts plots showing that different preparation conditions cluster together by sample, using Uniform Manifold Approximation and Projection (UMAP) projections of Visium transcriptomic data, wherein points represent spots.
Figure 1I:
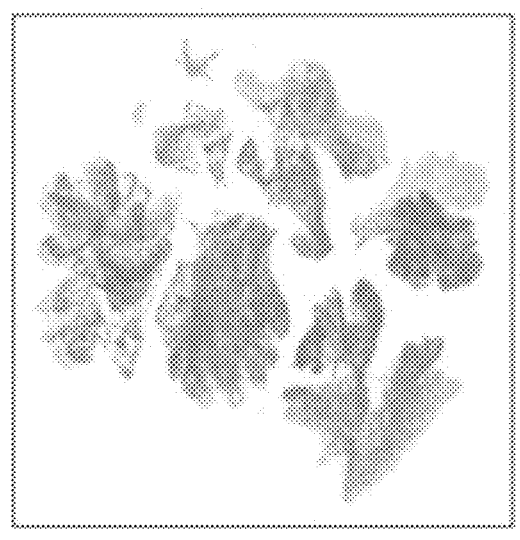
Figure 1I:
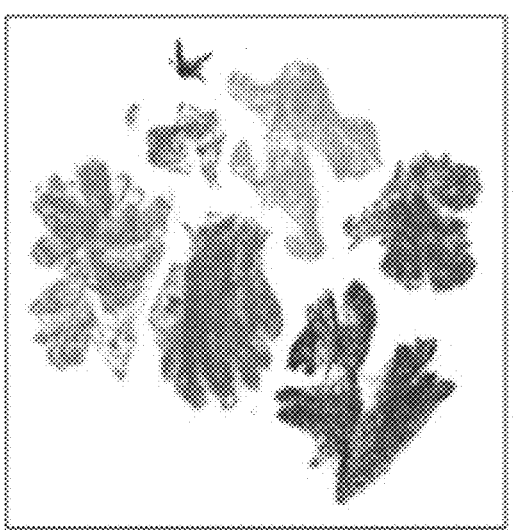
Figure 1J:
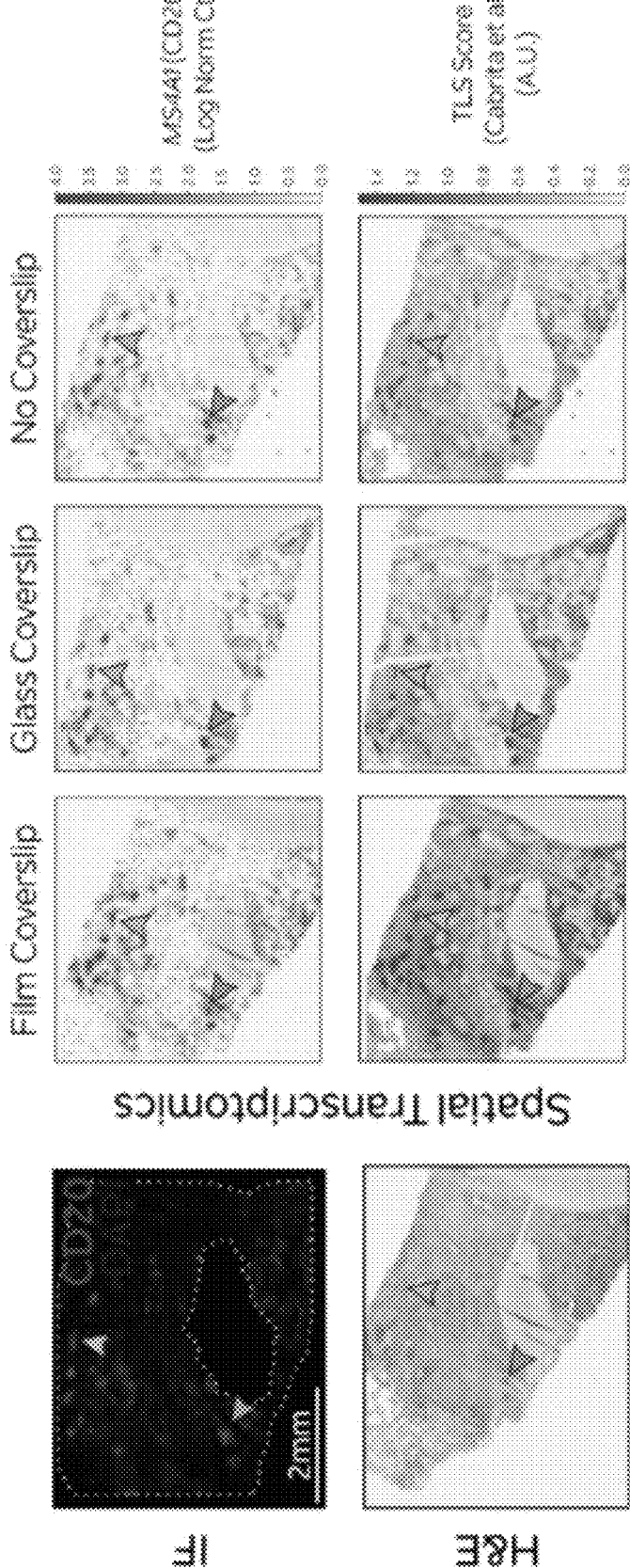
FIG. 1J depicts plots showing that Visium gene expression patterns are consistent across preparations, using IF, H&E and ST data collected from different sections of the same sample, wherein arrowheads indicate regions of high B-cell abundance that can be observed across all data modalities and sample preparation conditions.

The outcome of the study demonstrated that key quality control metrics and spatial biomarkers are consistent across all three sample preparation conditions, and using different H&E staining protocols, as shown in FIG. 1H, FIG. 1I and FIG. 1J, respectively. Specifically, FIG. 1H depicts plots depicting Visium quality control metrics that are consistent across sample preparations, wherein P-values represent results of Kruskal-Wallis tests. FIG. 1I depicts plots showing that different preparation conditions cluster together by sample, using Uniform Manifold Approximation and Projection (UMAP) projections of Visium transcriptomic data, wherein points represent spots. FIG. 1J depicts plots showing that Visium gene expression patterns are consistent across preparations, using IF, H&E and ST data collected from different sections of the same sample, wherein arrowheads indicate regions of high B-cell abundance that can be observed across all data modalities and sample preparation conditions.

Figure 1K:
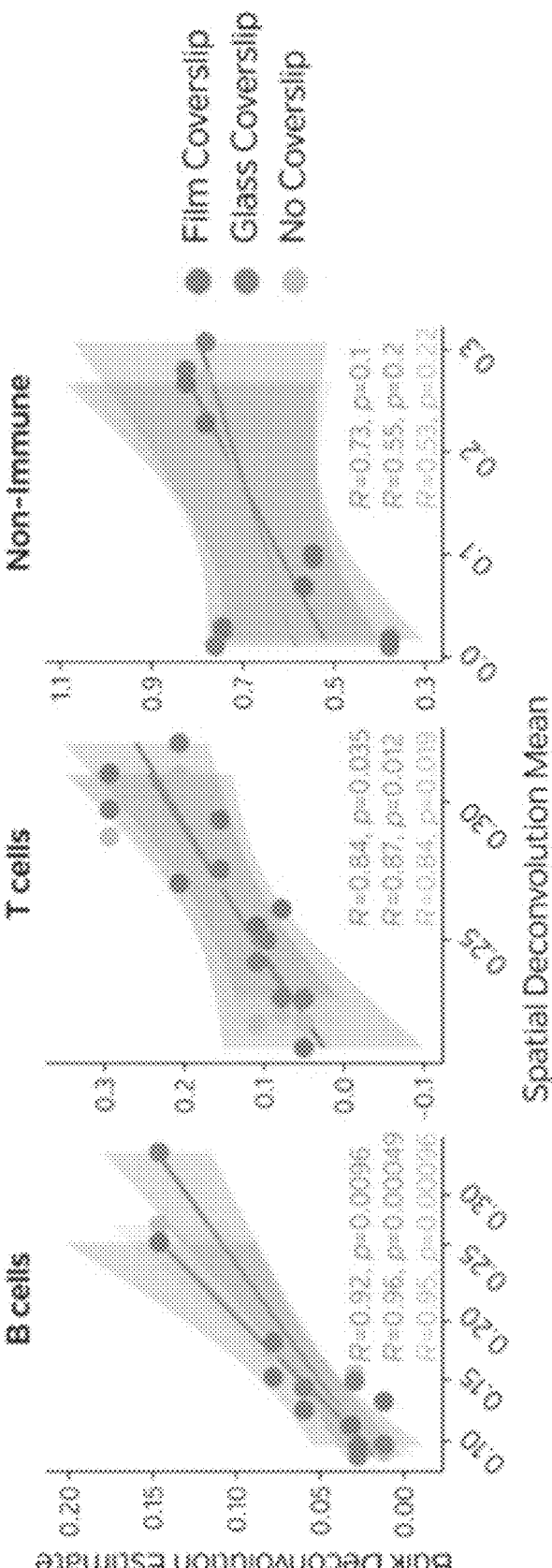
FIG. 1K depicts charts demonstrating that immune deconvolution estimates are consistent across preparations, wherein points represent individual samples, and R and p values indicate the results of a Pearson test for correlation between bulk and spatial values.
Figure 1L:
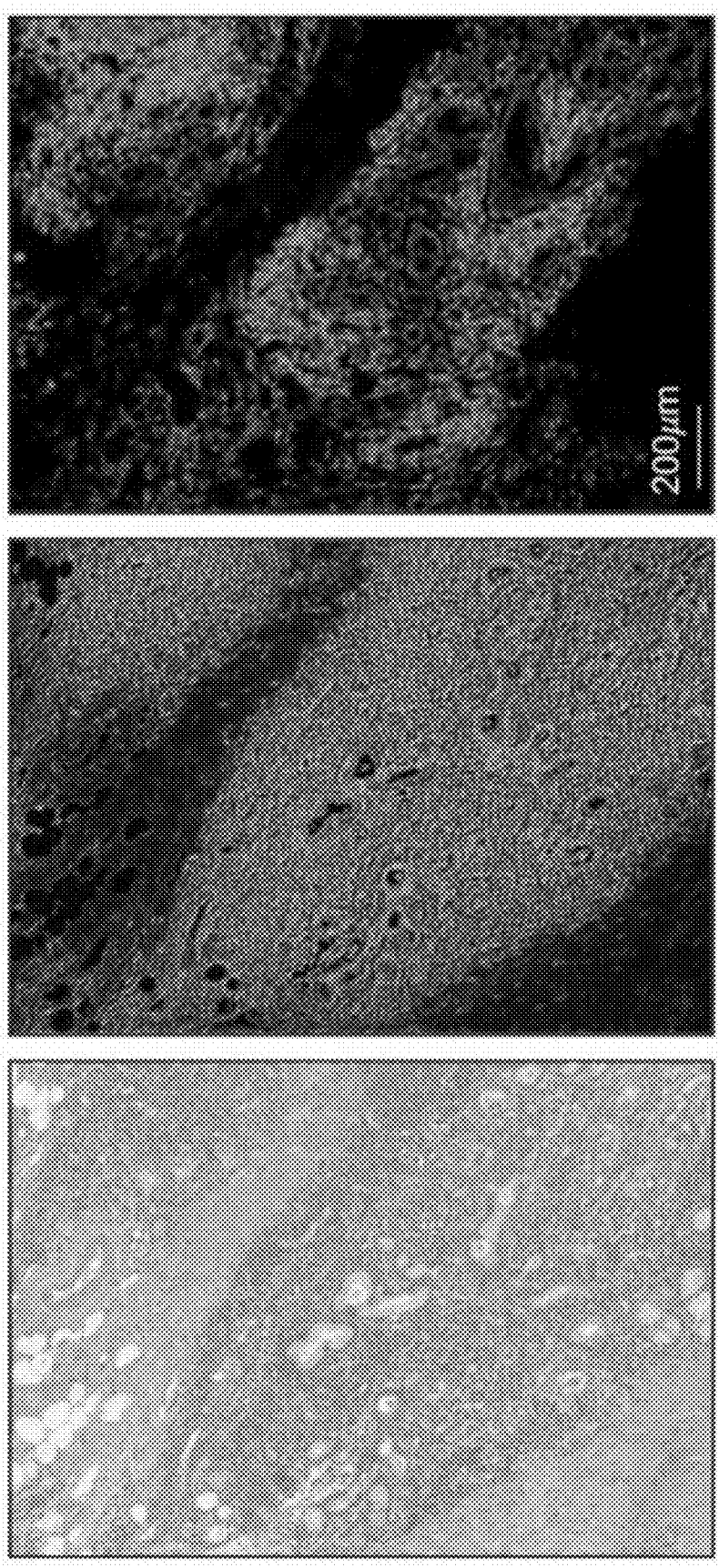
FIG. 1L depicts gene maps demonstrating that computational super-resolution inference agrees with IF.

When comparing deconvolution results between bulk and spatial transcriptomics we observe correlations for many cell types despite differences in sample preparation, supporting the idea that bulk and spatial samples contain complementary transcriptomic information, as depicted in FIG. 1K. However, the present techniques also demonstrate that within samples, many of the correlations observed in bulk do not show a strong spatial correlation. These comparisons indicate the importance of considering spatial context when studying the tumor immune microenvironment. Spatial biomarkers agree between super-resolution ST and multiplex IF across sample preparation conditions, as shown in FIG. 1L.

Specifically, FIG. 1K depicts charts demonstrating that immune deconvolution estimates are consistent across preparations, wherein points represent individual samples, and R and p values indicate the results of a Pearson test for correlation between bulk and spatial values. FIG. 1L depicts gene maps demonstrating that computational super-resolution inference agrees with IF. Super-resolution gene maps (center) may be computationally generated at an increased resolution of ~1.5 μm/pixel by combining ST data at spot resolutions of 50 μm/pixel with H&E images (left). Lymphocytes (green) can be distinguished from tumor cells (red), correlating with IF (right).

When comparing deconvolution results between bulk and spatially-resolved methods, the study observed modest correlations for many cell types despite the differences in sample preparation, supporting the notion that bulk and spatial samples contain complementary transcriptomic information. However, within samples, the study found that many of the correlations observed in bulk do not show appreciable spatial correlation. These deconvolution comparisons indicate the importance of considering spatial context when studying the tumor immune microenvironment. Finally, the study found an agreement between super-resolution ST and multiplex immunofluorescent (IF) images across key spatial biomarkers. The present techniques may be used to infer cell types and gene matrix mapping on cells adjacent to the spatial transcriptomics capture region.

A registered field of view may be used to compare a select number of stains from multiplex immunofluorescent (IF) images to corresponding super-resolved ST (spatial transcriptomics) maps. These regions may be registered by eye for visualization purposes and may not need computational registration. In some aspects, super-resolved ST maps may be much lower resolution (~3 um/pixel) compared to multiplexIF images. In some aspects, the present techniques may be used to obtain a quantitative measure of the agreement between multiplexIF images and the super-resolution images. This may require computational registration between the two images, wherein agreement is calculated using SSIM (structural similarity index measure).

Specifically, modifications may be made to the training pipeline discussed herein. In some aspects, modifications may be performed to the pipeline to make it forward-compatible with updates to the 10× Genomics data generation pipeline. The new CytAssist data generation pipeline, for example, may include additional feature columns for antibody capture in addition to gene expression. Some legacy tools (e.g., xFuse) incorrectly overwrite the gene expression columns with the values in the antibody capture columns, so the xFuse dataloader may be modified to filter out the antibody capture columns entirely. Data generated at 10× Genomics measures the X-Y position of the Visium spots in the coordinate system of the high resolution whole slide images (WSIs) taken at 10× Genomics. In order to make legacy trained models compatible with proprietary images, the present techniques may include translating those coordinates onto the corresponding proprietary WSIs scans of the same slides. Data generated at 10× Genomics may use the larger 11×11 mm capture areas instead of the 6.5×6.5 mm capture areas that legacy models were originally designed for. In order to manage GPU memory constraints, the present techniques may include dividing proprietary images into many (e.g., 4) smaller regions roughly corresponding to a 6.5×6.5 mm area for running inference.

In some aspects, further modifications to legacy modeling systems may be made, to enable those systems to be compatible with large-scale training on proprietary ST data (e.g., generated using CytAssist). Specifically, the above modifications were the bare minimum needed to make legacy code compatible with large-scale training on proprietary-generated CytAssist spatial transcriptomics data. Several additional modifications may will be desired in order to make the process of training legacy models feasible in the future, especially as the proprietary database of data grows.

In some aspects, the present techniques may optimize GPU memory usage during model inference, avoid over-allocation of memory even when training completes successfully. In particular, it has been observed that a model runs out of machine memory during training time. Diagnostics have suggested that It a cache is not being cleared. The present techniques may be used to find that cache and clear it. In some aspects, the present techniques may include allowing dataloader to train on a subset of Visium spots listed in the feature barcode matrix file. A tissue segmentation/masking module may be improved to enable use with proprietary stain intensities. In some aspects, the present techniques may implement more detailed control of gene and spot filters during training, and/or allow training on pre-specified metagenes. This may facilitate learning of spatially variable gene expression of certain markers, when the underlying tissue/H&E does not have obvious morphological differences. In some aspects, this involves determining the metagenes in advance (e.g., using non-negative matrix factorization (NMF)) and being able to force xFuse to use these metagenes as a warm starting point for training.

Exemplary Gene Filtering Strategies

In some aspects, in order to optimize legacy (e.g., xFuse) models, and maximize the accuracy of the output super resolution maps, the present techniques may define a set of techniques to filter the ST data before these are used to train those models. In one aspect, the present techniques may include dropping spots with less than X counts and with > than 99th percentile of counts. This may be done to remove noisy RNA expression measurements that may negatively affect model training. By applying this filter, only spatial RNA expression data that is considered most reliable is kept. In another aspect, the present techniques may include dropping genes detected in fewer than 10 spots. Genes that are poorly expressed at the spatial level from the list of genes used to train the model may be removed. In some aspects, genes with low and high total counts may be removed. Genes with low counts may not be reliable as they do not provide enough information to train the model. In some aspects, a threshold based on the statistics of the counts across the spots (e.g. 10th percentile or 1000 counts) may be selected for removal. Similarly, the present techniques may include excluding genes whose counts are higher than the 99th percentile, as this measure may be artifactual and not reliable. In some aspects, the present techniques may include dropping genes with low spatial variability. For example, genes with low variance across the tissue may have a poor signal-to-noise ratio and therefore impair model training. The present techniques may exclude those that are below a given threshold or percentile as above.

The present techniques may perform manifold embedding and clustering based on transcriptional similarity. Specifically, the present techniques may include performing PCA, NMF or t-SNE to visualize the spatial expression patterns of groups of genes and identify clusters of genes that are co-expressed in specific regions of the tissue. The present techniques may perform clustering in gene expression space (k-means, hierarchical clustering, Louvain clustering or NN embeddings) to group genes that have similar spatial expression patterns and are specific to particular cell types or regions of the tissue. The present techniques may visualize gene clusters in spatial dimensions to define phenotypes and gain insights into tissue organization and cellular communication.

In some aspects, the present techniques may perform characterization of immune phenotypes from the gene maps for tumor-infiltrating lymphocyte/Slide structuring. In particular, as a potential application of ST and/or xFuse in the context of slide structuring and histogenomics models.

Immune phenotypes may be determined based on cell types classified by a pathologist or by a cell classification model. Gene maps produced by the output of the ST pipeline and/or by xFuse to cluster different immune phenotypes that are correlated to immunotherapy response.

These results demonstrate that clinical archival FFPE samples yield high interassay reliability and correlation via the sequencing platform. These results were consistent through three different H&E staining protocols and findings were consistent when super resolution deconvolution was utilized which further strongly correlated with high-resolution multiplexed IF. The findings of this study demonstrate the feasibility and translational utility of ST to discover spatial signatures and the cellular context in retrospective clinical cohorts to empower discovery and translational efforts in precision oncology and therapeutic development.

Validation Example 2

In another aspect, the present techniques may include training two different the low-to-high resolution ST model models from scratch; a first corresponding to pancreatic ductal adenocarcinoma (PDAC) patients including four slides of training data; and a second corresponding to lung cancer patients including two slides of training data. Future studies are envisioned using more (e.g., 20 or more) slides.

The study may include a validation data set comprising colorectal cancer with adenocarcinoma diagnosis comprising 58 slides, having 167 slide field-of-views (FOVs) and a tumor infiltrating lymphocytes (TIL) breast cancer with adenocarcinoma diagnosis cohort comprising 45 slides, having 217 slide FOVs. Both the colorectal cancer and breast cancer slides may include cell-level pathologist annotations (e.g., one annotator per FOV).

One motivation for selecting these two cohorts is that the pancreatic cancer model was trained on adenocarcinoma patients. Thus, to replicate that, the study was intentionally parameterized with adenocarcinoma diagnosis patient data to limit differences caused by different cancer types.

Exemplary Cell Segmentation Pipeline Aspects

Figure 2A:
FIG. 2A depicts a cell segmentation map, according to some aspects.
Figure 2A:
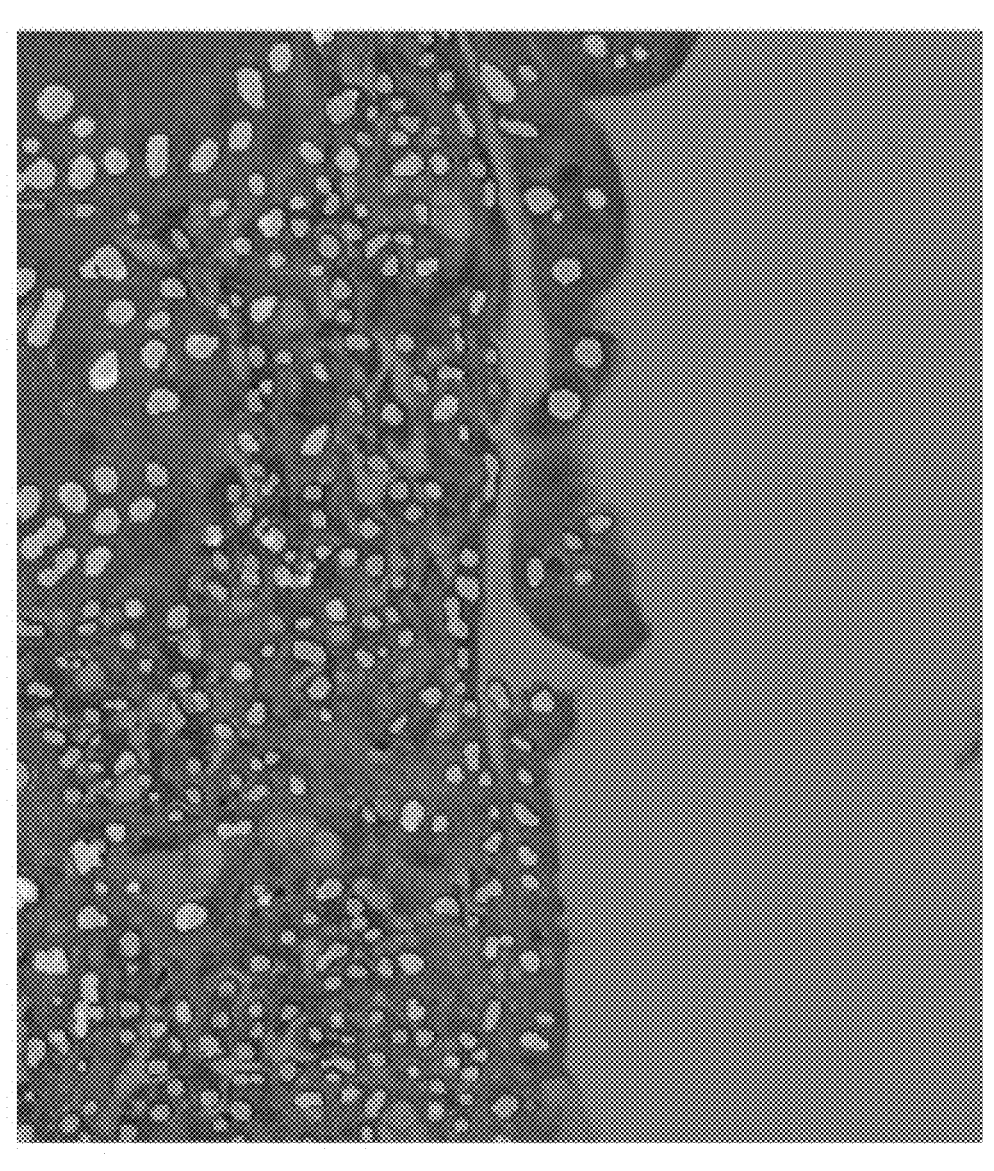
Figure 2B:
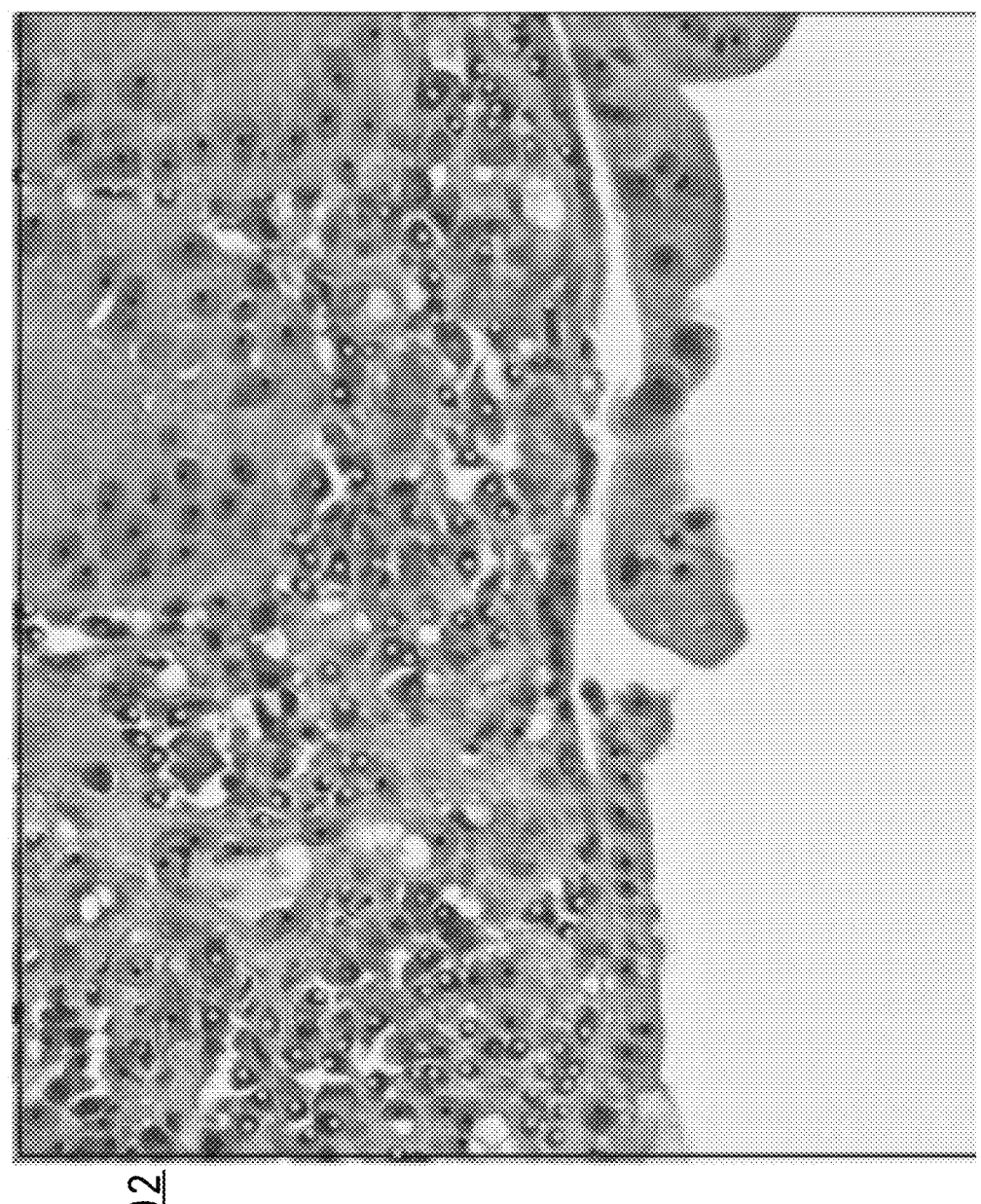
FIG. 2B depicts pathologist annotation images, according to some aspects
Figure 2C:
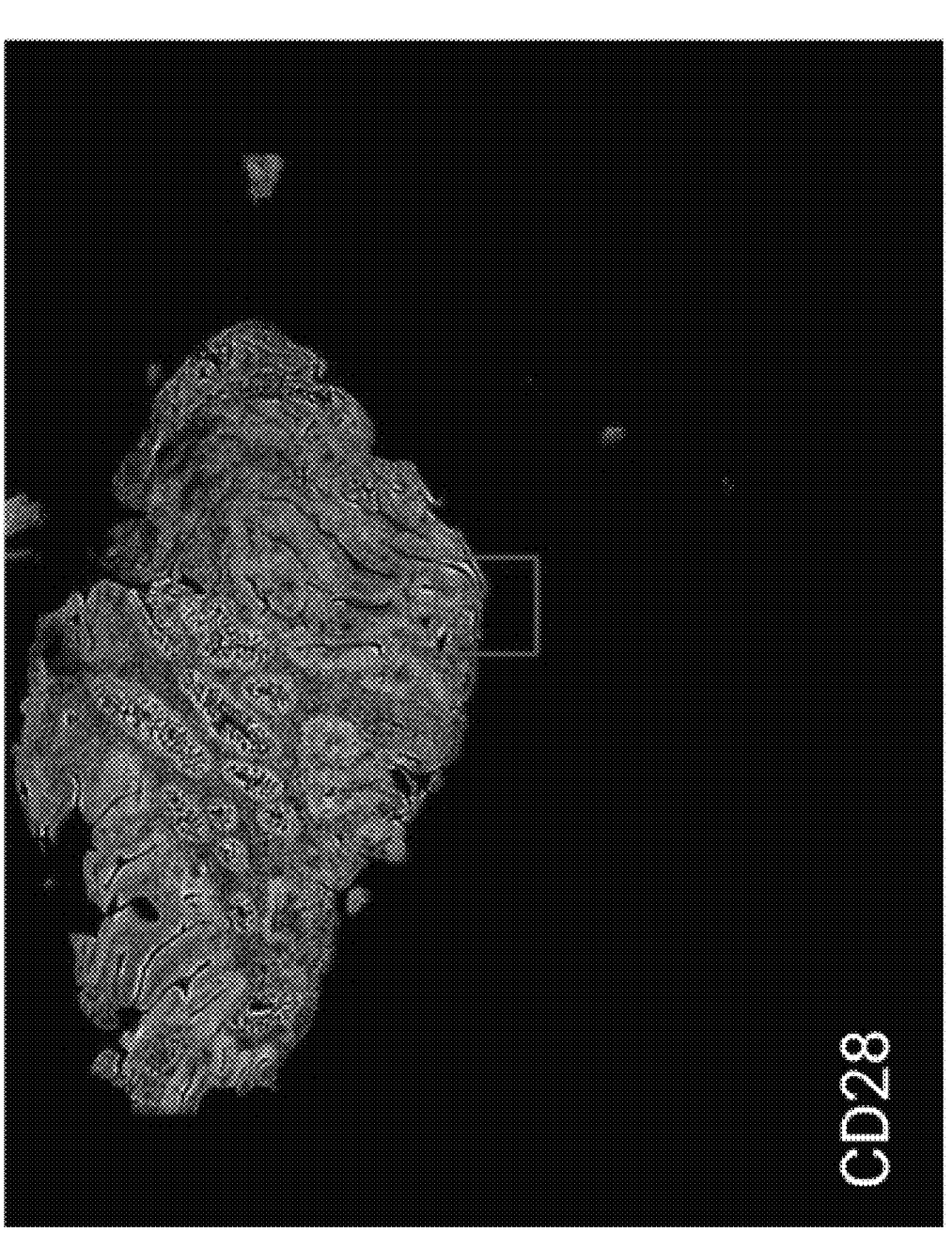
FIG. 2C depicts a zoomed out view of a gene (CD28).

FIGS. 2A-2C depict images used in a cell segmentation pipeline of the present techniques, according to some aspects. The present techniques may include producing, for each FOV, a cell segmentation map 200 using a digital pathology segmentation model, as shown in FIG. 2A. In some aspects, the digital pathology segmentation model may be implemented using other cell segmentation techniques (e.g., those of U.S. Pat. No. 10,991,097; "ARTIFICIAL INTELLIGENCE SEGMENTATION OF TISSUE IMAGES"; incorporated by reference herein in its entirety for all purposes). It will be appreciated by those of ordinary skill in the art that other cell segmentation pipelines may be suitable for use, in some aspects.

The present techniques may include receiving pathologists' annotations 202 from a digital pathology viewer (e.g., as in U.S. Pat. No. 10,957,041; "DETERMINING BIOMARKERS FROM HISTOPATHOLOGY SLIDE IMAGES" and U.S. Pat. No. 11,348,239; "PREDICTING TOTAL NUCLEIC ACID YIELD AND DISSECTION BOUNDARIES FOR HISTOLOGY SLIDES"; both herein incorporated by reference for in their entireties, for all purposes), as shown in FIG. 2B. For example, the cells in specific FOVs may be labeled as either tumor cells, or one of three normal cell types (lymphocytes, macrophages, fibroblasts). In some aspects, other cell types/labels may be used. It will be appreciated by those of ordinary skill in the art that FIG. 2A corresponds to FIG. 2B. The cells of FIG. 2A have been annotated with pathological information.

FIG. 2C depicts a zoomed out view of a gene (CD28) including a region 204 that corresponds to the cell segmentation map 200 of FIG. 2A and the pathologists' annotations 202 of FIGS. 2A and 2B, respectively.

Exemplary Super-Resolved Gene Expression Heat Map Aspects

In some aspects, the present techniques may include using the low-to-high resolution ST model to produce a gene expression heat map for an entire padded image, by using the low-to-high resolution ST model outputs. The present techniques may further searching the zoomed out the low-to-high resolution ST model image to locate the FOV that matched the histology FOV with histology slide images.

Figure 3A:
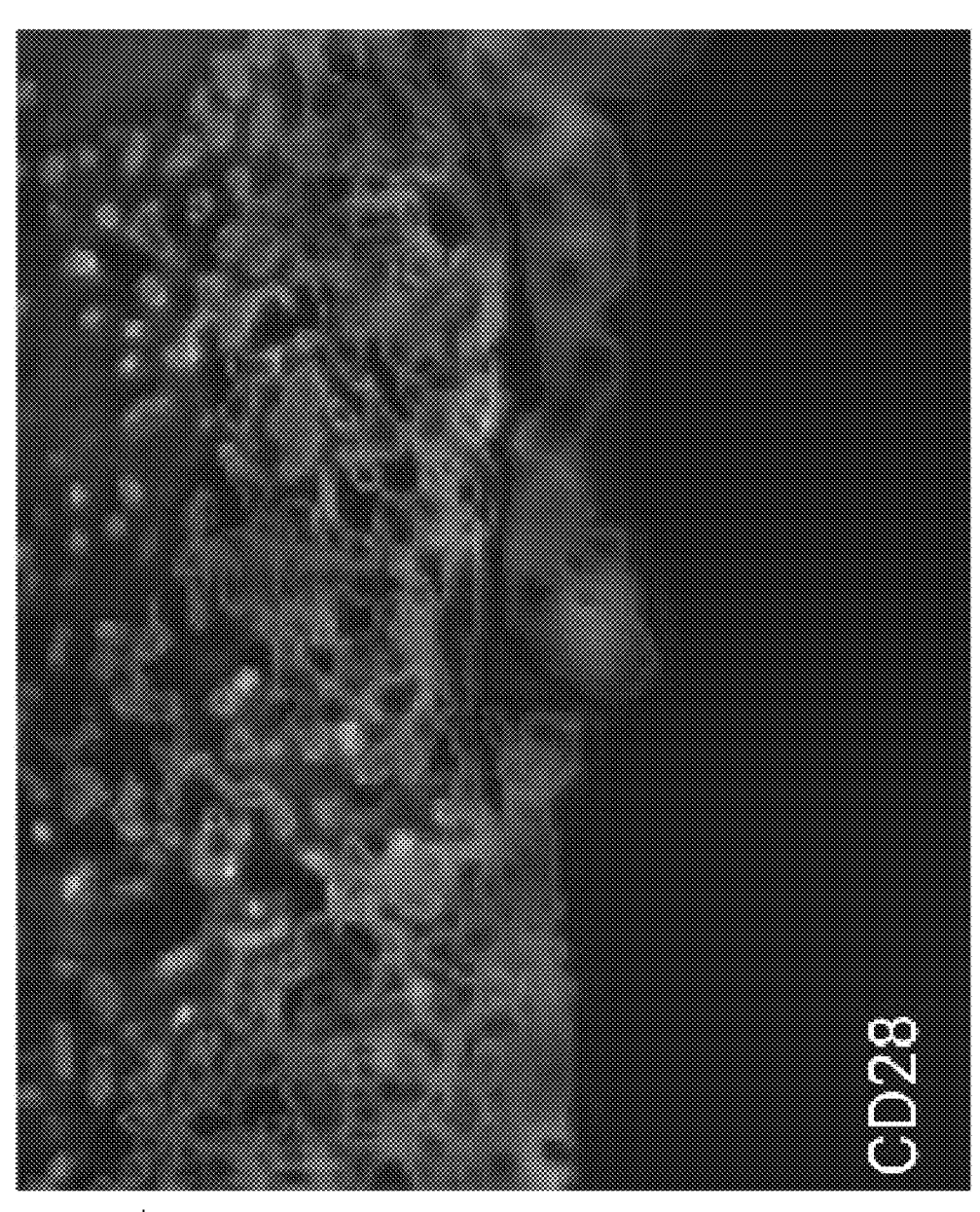
FIG. 3A depicts an exemplary super-resolved gene expression.
Figure 3B:
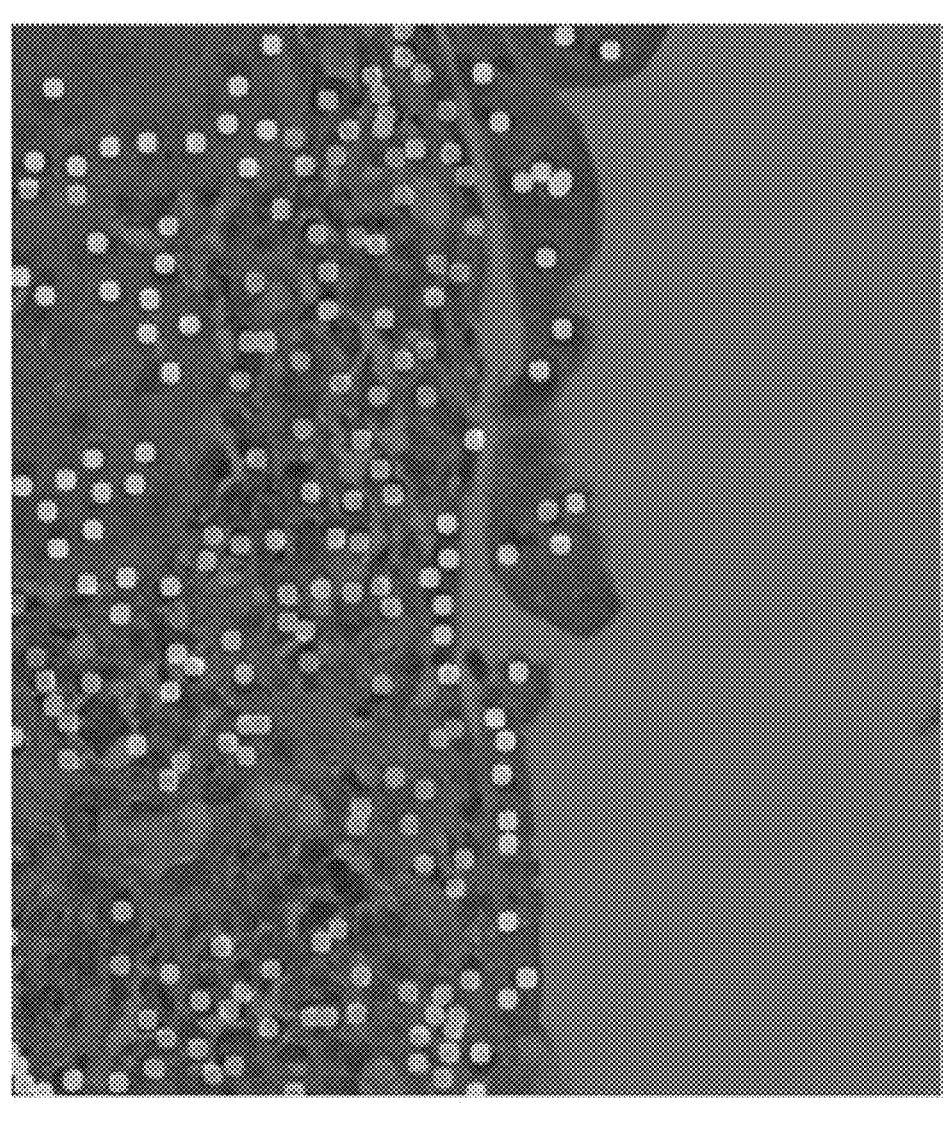
FIG. 3B depicts a resized cell segmentation map including predicted gene expression per cell, according to some aspects.

For example, FIGS. 3A and 3B depict, respectively, an exemplary super-resolved gene expression 300, and a resized cell segmentation map 302 including predicted gene expression per cell, according to some aspects. The super-resolved gene expression 300 and the resized cell segmentation map 302 correspond to the region 204 of FIG. 2C, the pathologists' annotations 202 of FIG. 2B and the cell segmentation map 200, in some aspects.

The present techniques include matching the resized cell segmentation map 302 by locating the FOV matching the histology FOV in the zoomed out image of the gene. This cropped image may be generated, wherein the generated image includes super resolved expression of the gene, as depicted in FIG. 3A. The present techniques may include matching the cropped image including the super resolved expression of the gene with resized cell segmentation contours to generate a predicted gene (e.g., CD28) expression per cell by aggregating the gene expression values within each cell contour, as depicted in FIG. 3B. This process may be repeated for each selected gene, to generate a cell by gene co-matrix there. The present techniques may include performing cell type mapping to obtain predicted cell types, and comparing the predicted cell types against pathologists annotations that serve as the ground truth cell labels to evaluate performance of the cell generation and heat map generation pipelines.

In some aspects, matching the images in FIGS. 2A-3B may be performed by coordinate tracking. For example, a first set of coordinates of the map in FIG. 2C, generated by the low-to-high resolution ST model may be a map at 40× magnification in relation to the original HE image, may be tracked. Further, a second set of coordinates in 40× magnification of the cell segmentations in the original HE image may be tracked. An obstacle overcome to obtain and track the coordinates is that conventional low-to-high resolution modeling techniques may internally pad images before scaling. This is not necessarily perceptible, and is not immediately apparent without dissecting the code of the upstream low-to-high resolution modeling. Furthermore, these changes to padding are non-deterministic (e.g., change with every image) and in some aspects, require the use of an image mask to the area of the annotated region, and sending both the masked and unmasked version of the image into the low-to-high resolution ST model, so that subsequent processing can match the output of the low-to-high resolution ST model back to the original input image.

In particular, the coordinate tracking step was used during training to match the coordinates of cell segmentations in the original histology image coordinates in scaled images of the low-to-high resolution ST model, by feeding into a scaling function of the low-to-high resolution ST model an image that is either a crop of the original image or version of the original image with a specific rectangular field of view masked out (e.g., in black). Doing so enables calculation of coordinate conversions (coordinate tracking) because a height and/or a width of the scaled image or the corners and boundaries of the rectangular black mask in the scaled image may be detected.

In some aspects, other methods of image registration known in the art may be used (for example, template matching). The present techniques may include inferring cell types and gene matrix mapping on cells adjacent to the spatial transcriptomics capture region.

Exemplary Gene-Cell Matrix to Cell-by-Cell Type Mapping Aspects

Figure 4A:
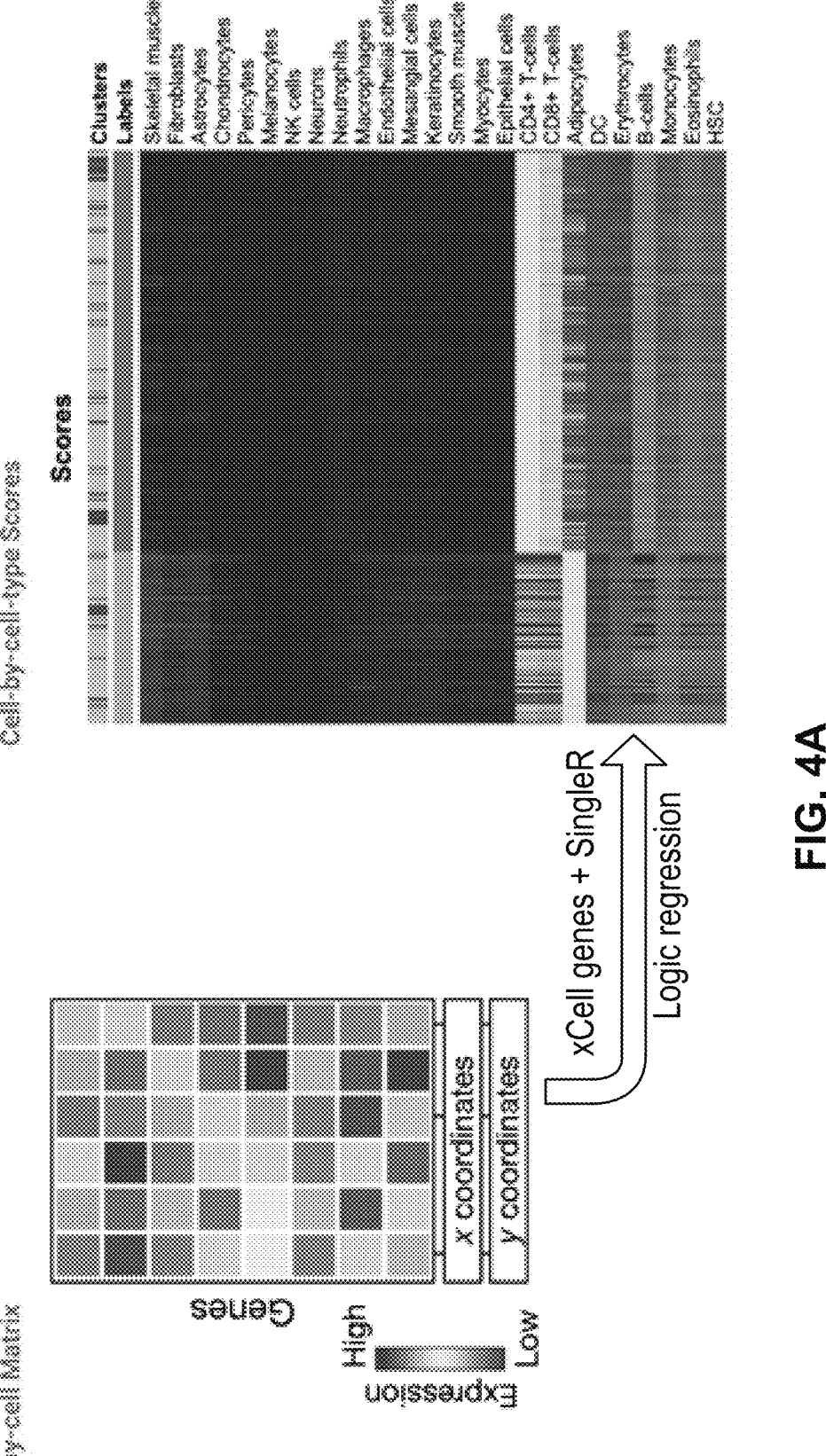
FIG. 4A depicts an exemplary mapping of a cell by gene co-matrix onto cell types, according to some aspects.

FIG. 4A depicts an exemplary mapping of a cell by gene co-matrix onto cell types, according to some aspects. As discussed above with respect to FIG. 3A and FIG. 3B, the present techniques may include producing a cell by gene co-matrix. This co-matrix is visualized on the left side of FIG. 4A. The present techniques may include mapping the cell by gene co-matrix onto certain cell types, to obtain a cell by cell matrix, as shown on the right hand side of FIG. 4A.

In some aspects, the present techniques may perform the mapping using a regression (e.g., a logistic regression), for example having five-fold validation predicting seven cell types. In some aspects, class balancing may be used during training.

As discussed below with respect to FIG. 4B, in some aspects, the present technique may include selecting one or more genes from the xCell paper (see above, Background) and applying SingleR (see above, Background), initially intended for labeling/annotating single cell RNA seq gene expression data. It will be appreciated by those of ordinary skill in the art that to save memory, the present techniques may include instructing the computer to save only the cell by gene matrix instead of each the low-to-high resolution ST model gene heat map.

Figure 4B:
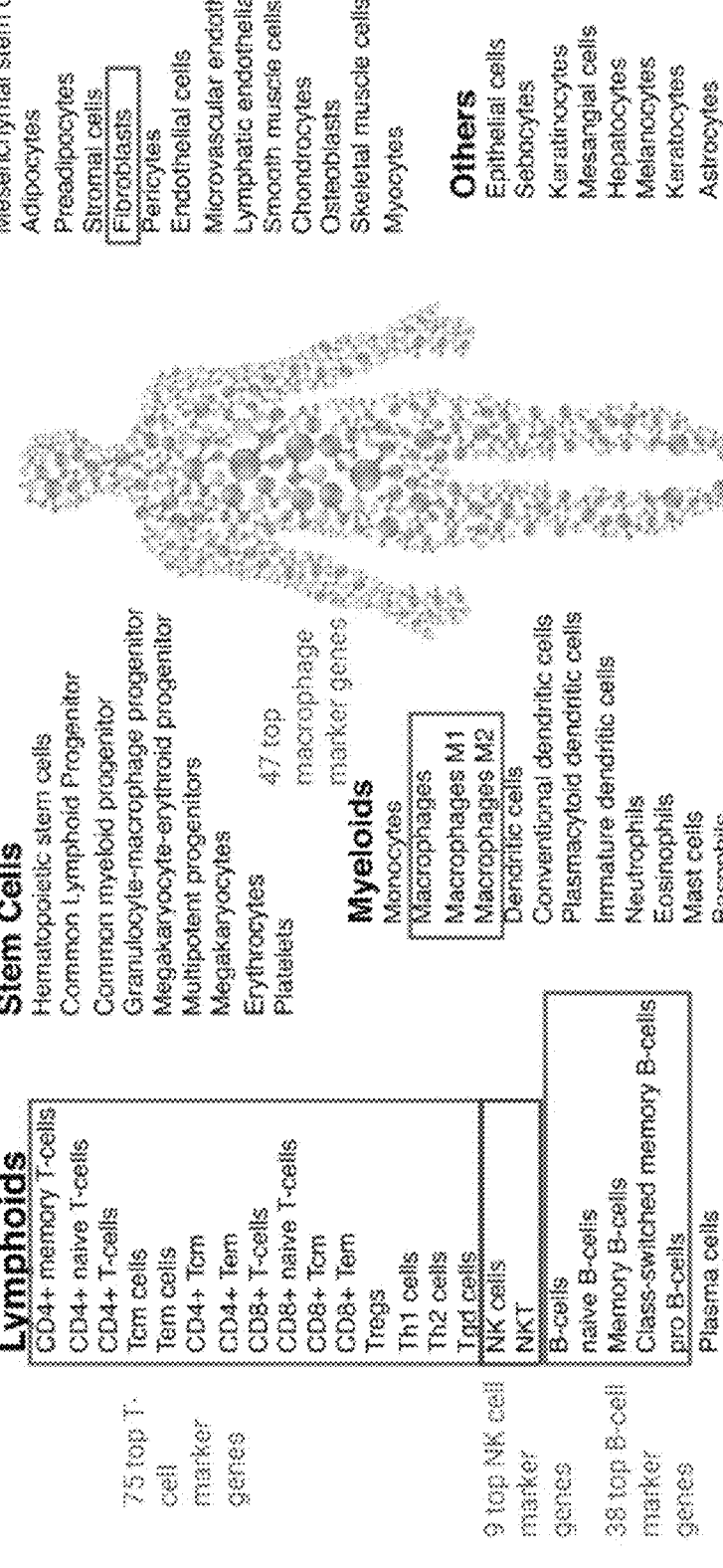
FIG. 4B depicts marker genes selected from xCell, according to some aspects.

FIG. 4B depicts marker genes selected from xCell, according to some aspects of the present techniques. While logistic regression may be used in some circumstances, those of ordinary skill in the art will recognize that there are several hundred FOVs may be of interest for inferential purposes. Those of ordinary skill will further recognize that running the low-to-high resolution ST model inference engine to produce gene expression maps for more than 2000 gene expression values provided for each location by an ST/sequencing platform may be computationally expensive, and/or prohibitive, and that it may be advantageous to limit the computational problem size.

Therefore, the present techniques may include selecting a subset of marker genes of the cell types of interest, as depicted in FIG. 4B. In some aspects, the present techniques may select these marker genes so as to maximize informativeness in differentiating between selected cell types. The xCell paper discusses manually collected and curated gene expression profiles from multiple reference datasets and includes a large list of cell type specific marker genes.

The present techniques may include automatically processing this curated data. For example, the present techniques may include aggregating one or more T-cell subtypes and selecting a number (e.g., 75) of top T-cell marker genes, a number (e.g., 9) of top natural killer cell marker, and aggregated B cell to select a number (e.g., 38) of top B-cell marker genes, a number (e.g., 47) of top macrophage marker genes, a number (e.g., 31) of top fibroblast marker genes, etc. for a total (e.g., 200) of genes used to infer cell types. Of course, the present techniques may include instructions for selecting more or fewer genes from each subtype may be automatically selected, in some aspects.

To select the top markers, for each aggregated list, the present techniques may count how many occurrences of the marker gene are in the list and select the genes that occurred the greatest number of times. In various embodiments, genes selected in this manner may be the most robust reliable markers shared among the most cell subtypes.

Figure 4C:
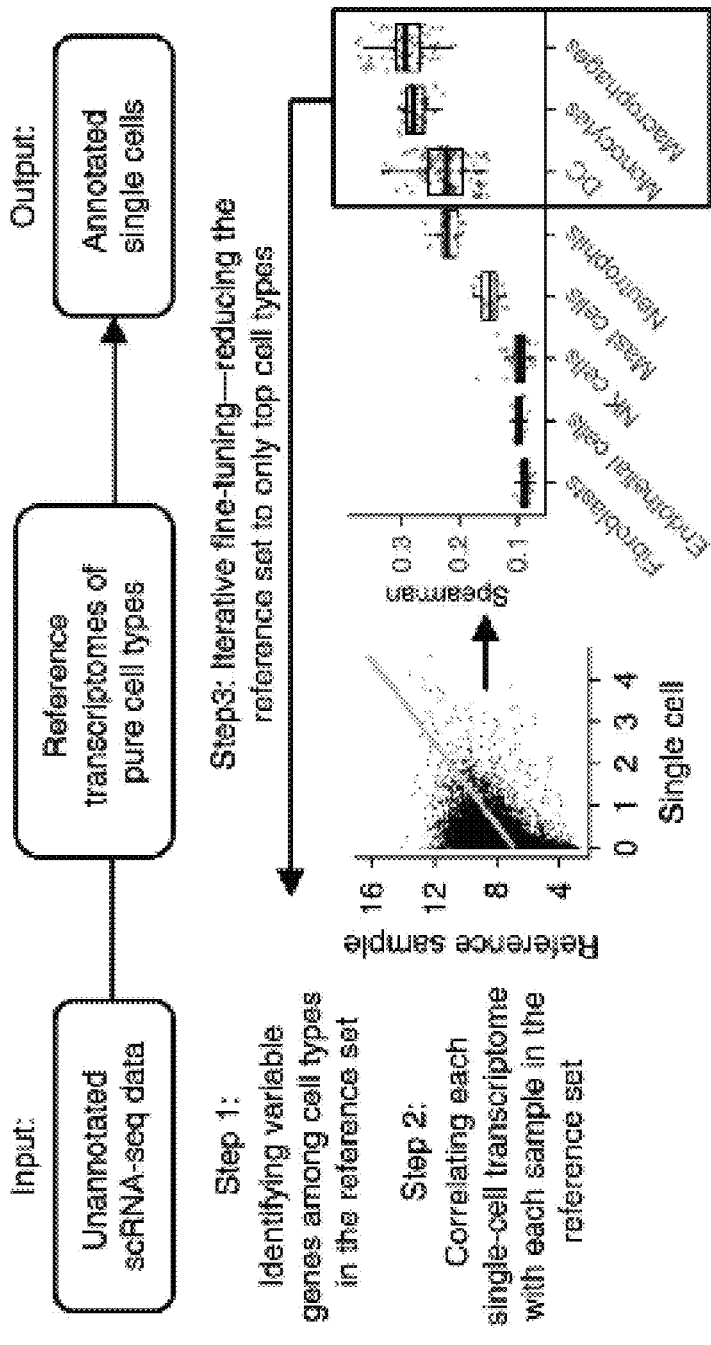
FIG. 4C depicts an example of mapping gene expressions for each cell to a cell type using SingleR, according to some aspects.

For example, each cell type may include several sub-types (e.g. there are 9 subtypes of B-cells). Further, each subtype may list a set of genes. For each larger class (e.g. B-cells or lymphocytes) the present techniques may include counting a number of subtypes listed in each gene, and selecting a set of genes most well-represented in a number of subtypes to include in a final list corresponding to the larger class. Other techniques for selecting a set of marker genes for a cell class are envisioned. For example, in some aspects, the set of marker genes may include generating all gene maps and training the cell classification model on all those genes, such that the model performs the gene selection process during the training process FIG. 4C depicts an example of mapping gene expressions for each cell to a cell type using SingleR. In general, SingleR works by identifying variable genes among cell types in a reference set, and correlating each single-cell transcriptome within each sample in the reference set, and finally, iteratively fine-tuning by reducing the reference set to only top cell types. In this last iterative fine tuning step, SingleR eliminates the least likely cell type one by one until the most likely cell type label for that cell is reached. In some aspects, the present techniques used blueprint/encode reference that was embedded in the SingleR package for reference data. That reference data included pure cell types (e.g., stroma and immune cells), so in some aspects, the present techniques may missing some tumor cell markers.

Figure 4D:
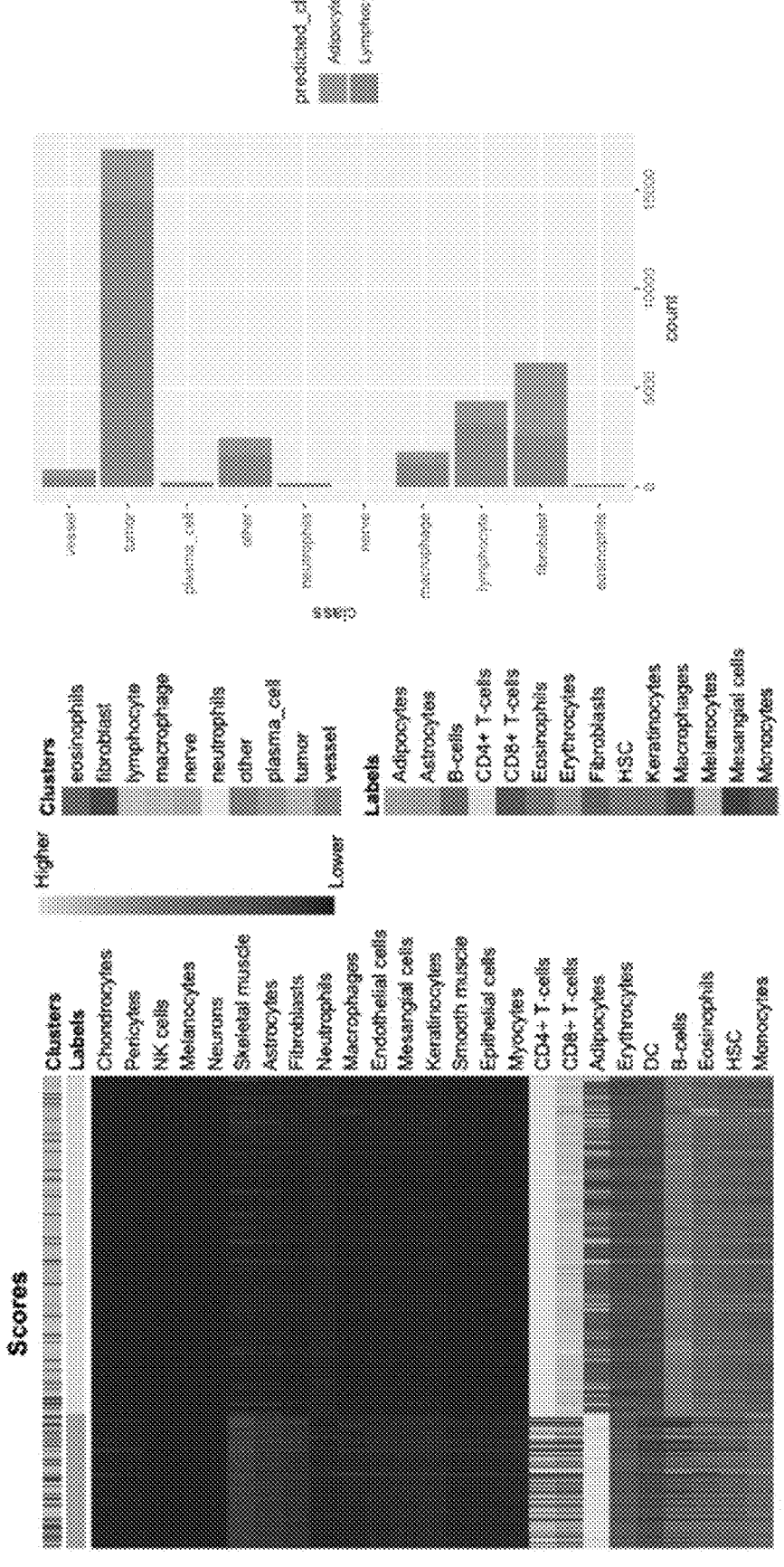
FIG. 4D depicts results for SingleR predicted labels for colorectal samples using the above-described model trained on lung cancer patients.

FIG. 4D depicts results for SingleR predicted labels for colorectal samples using the above-described model trained on lung cancer patients. FIG. 4D depicts correlation scores for each cell type, that show that there are two major classes of cells identified in the predicted labels, the first being adipocytes, and the second being CD4+ or CD8+ T-cells grouped together as lymphocytes, in the depicted example. Because there are no tumor cell labels in the reference set, the person of ordinary skill may wonder which label(s) to use corresponding to the tumor cells. Based on the distribution of the cell type labels identified, corresponding adipocytes are labeled to tumor cells. Lymphocytes are correlated lymphocytes and fibroblasts to fibroblasts.

FIG. 4E depicts a confusion matrix for the SingleR prediction (left) and logistic regression (right). Those of ordinary skill in the art will appreciate that the logistic regression performed better than the SingleR technique, in the depicted aspect. FIG. 4E also depicts a comparison (lower left corner) with results on a separate breast cancer cohort that was generated by the above-referenced digital pathology cell segmentation and classification model (e.g., in U.S. Pat. No. 11,348,239; "PREDICTING TOTAL NUCLEIC ACID YIELD AND DISSECTION BOUNDARIES FOR HISTOLOGY SLIDES", herein incorporated by reference in its entirety for all purposes).

In this aspect, a tumor F1 score of 0.73 was achieved for an internally stained slide and 0.76 for an externally stained slide. This result is comparable to the 0.74 observed in the logistic regression model (top right corner). The externally stained slides represent the closest comparison because the protocol of upstream sequencing platforms may be slightly different than the staining protocol described in (e.g., in U.S. Pat. No. 11,348,239), given different H&E reagents, autostainers, and scanners being used to generate the images used for the logistic regression results as opposed to the images used for the above-referenced digital pathology segmentation and classification and segmentation model.

FIG. 4F depicts a similar confusion matrix to FIG. 4E, for TIL breast cancer samples, according to some aspects of the present techniques.

Figure 4G:
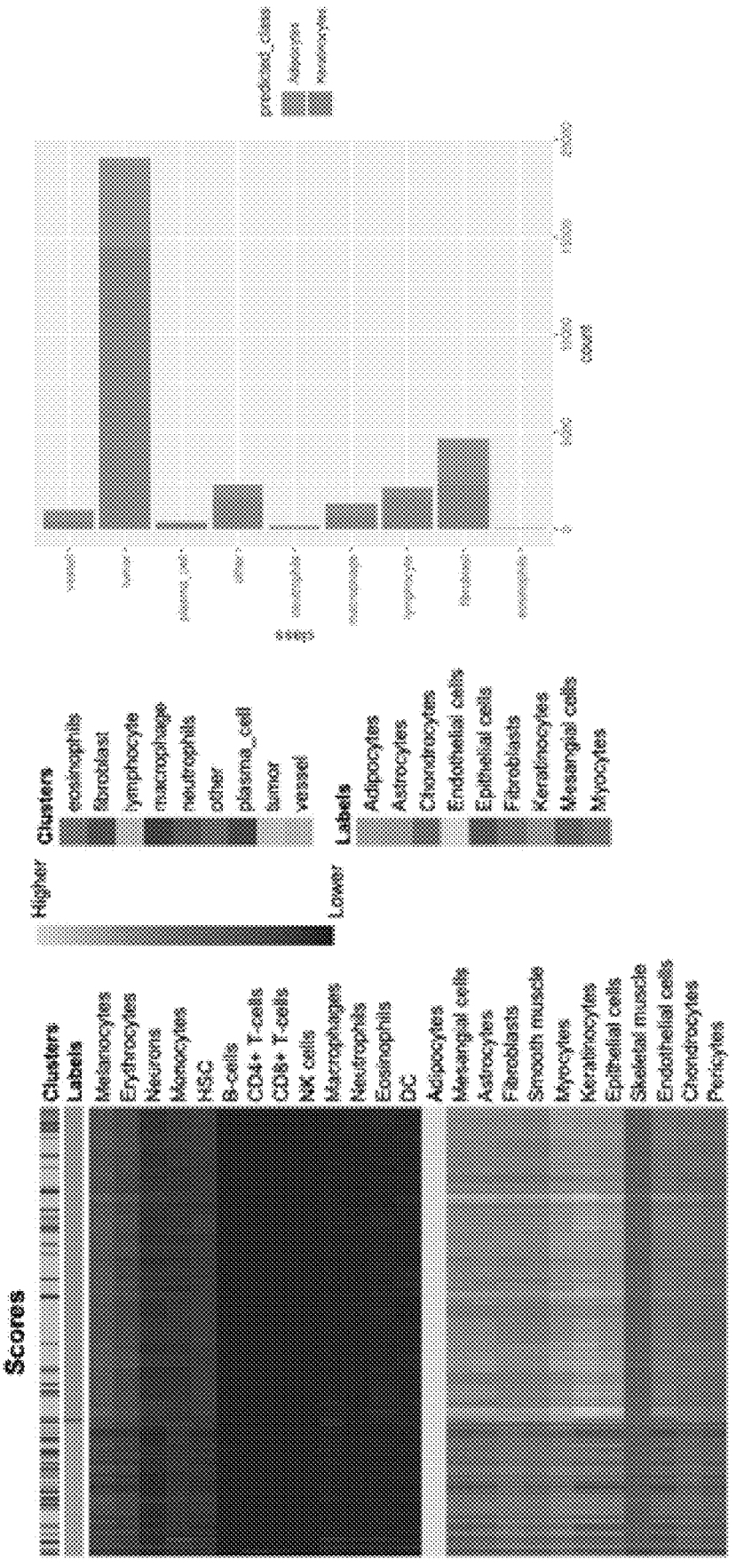
FIG. 4G depicts results for a model trained on PDAC.

FIG. 4G depicts results for a model trained on PDAC, according to some aspects. With respect to FIG. 4G, almost all cells here were correlated with adipocytes before the fine tuning step, and after the fine tuning step most were labeled as tumor cells. As shown, the adipocyte includes some enrichment of fibroblasts. For generating F1 score, the present techniques may include omitting adipocytes as the other label, and matching the tumor cells with keratinocyte label here.

FIG. 4H and FIG. 4I depict respective confusion matrices for the TIL BC samples/PDAC model and CRC samples/ PDAC model discussed above. In the depicted confusion matrix, many cells were labeled tumor cells. In the logistic regression, all the cells were labeled as tumor cells.

Future Directions

It should be appreciated that in some aspects, the present techniques may include licensing a dataset including super resolved gene maps from labeled data (e.g., to a pharmaceutical company). The present techniques may generate data that performs the function of ground truth labels for models (e.g., TIL models) and/or that functions as an augmented deliverable to incentivize spatial data licensing. In some aspects, the present techniques may include generating gene maps from unlabeled data. For example, the present techniques may be applied to perform direct lymphocyte classification and quantification. In some aspects, bulk RNA deconvolution may be performed to isolate tumor RNA. The present techniques include may using super resolved expression maps to train predictive models (e.g., TIL models) with greater accuracy, for example, to infer TIL subtype with greater accuracy based on latent morphologic features (e.g., in H&E images).

Lymphocyte quantification metrics may be very desirable to market participants, including pharmaceutical companies. In some aspects, the present techniques may be used without ST data (ISC expression) or the low-to-high resolution ST model. For example, histology images could be used with the above-described trained pipeline and bulk RNA seq data to generate super resolved expression maps.

In some aspects, validation plans may be compared to multiplexed IF gene expression and protein maps or pathologist annotated slides. This pipeline may be used for any H&E images even if the same scanner is not used consistently. For example, cancer type and/or scanner may affect performance. Training may be done with Leica scanned images, but each has a paired Phillips scanned image.

Example Computing Environment

Figure 5:
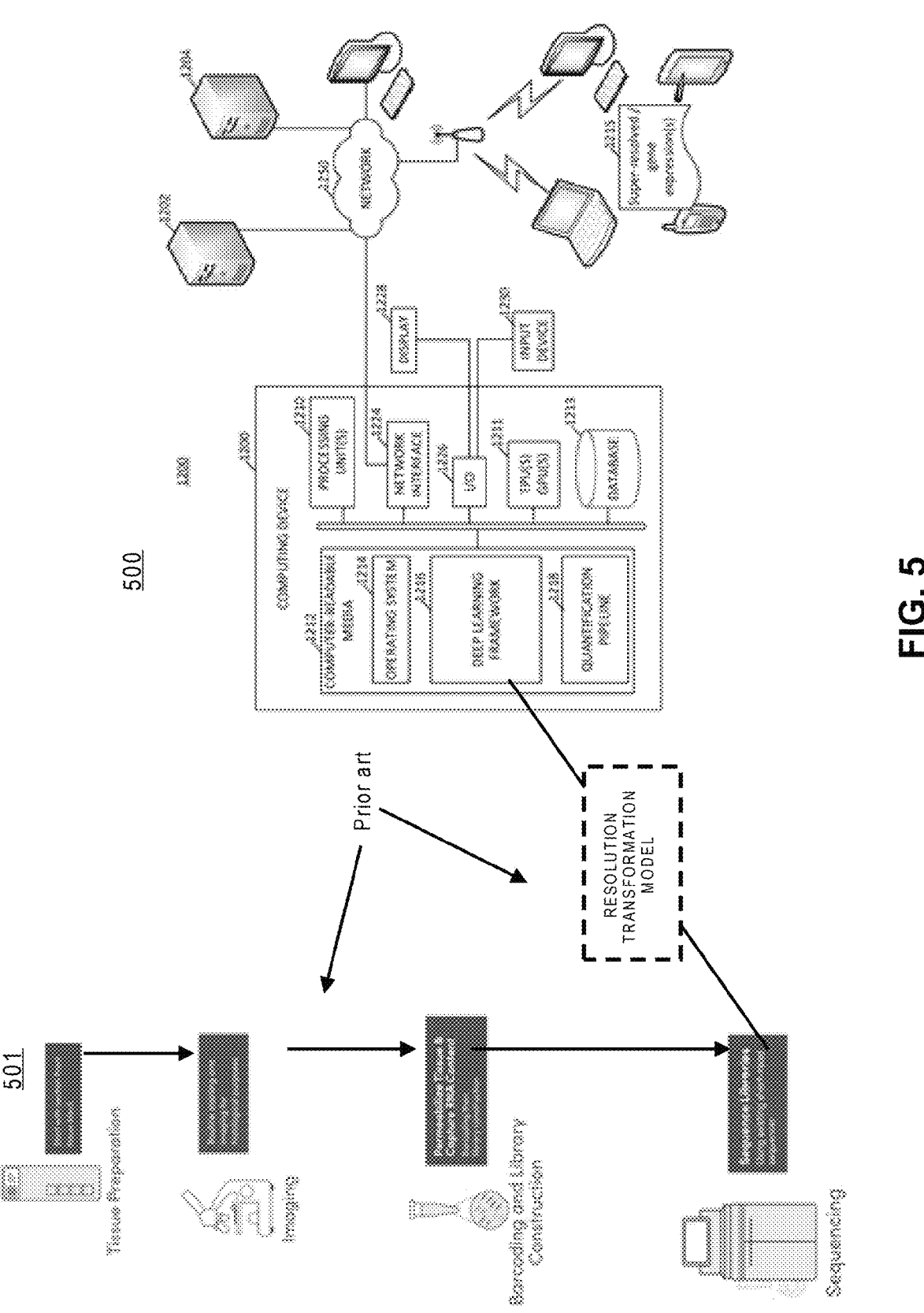
FIG. 5 depicts an example computing environment, according to some aspects.

FIG. 5 illustrates an example computing environment including an example computing device 500 for implementing the cell segmentation, annotation, heat map, and/or gene expression techniques of FIGS. 2A-2C, respectively. The computing environment may further include a spatial transcriptomics system 501. In some aspects the ST system 501 may be fully or partially implemented using a conventional ST technology.

As illustrated, the systems herein may be implemented on the computing device 500 and in particular on one or more processing units 1210, which may represent Central Processing Units (CPUs), and/or on one or more or Graphical Processing Units (GPUs) 1211, including clusters of CPUs and/or GPUs, and/or one or more tensor processing unites (TPU) (also labeled 1211), any of which may be cloud based. Features and functions described for the systems 100 and 500 may be stored on and implemented from one or more non-transitory computer-readable media 1212 of the computing device 500. The computer-readable media 1212 may include, for example, an operating system 1214 and the machine learning framework 1216 having elements corresponding to that of machine learning techniques discussed with respect to FIGS. 2A-4H. The machine learning framework 1216 may receive and process data directly from the conventional ST system 501, in some aspects.

These and other models herein are implemented as executable code, for example, in separate executable software applications, in one or more software applications, or in hardware, and in a single computing device or across multiple computing devices. The media 1212 may include a quantification pipeline 1218. More generally, the computer-readable media 1212 may store trained deep learning models, executable code, etc. used for implementing the techniques herein. The computer-readable media 1212 and the processing units 1210 and TPU(S)/GPU(S) 1211 may store image data, cell classification data, cell segmentation data and/or other data herein in one or more databases 1213.

The computing device 500 includes a network interface 1224 communicatively coupled to the network 1250, for communicating to and/or from a portable personal computer, smart phone, electronic document, tablet, and/or desktop personal computer, or other computing devices. The computing device further includes an input/output (I/O) interface 1226 connected to devices, such as digital displays 1228, user input devices 1230, etc. In some examples, as described herein, the computing device 500 generates a report as an electronic document 1215 that can be accessed and/or shared on the network 1250.

In the illustrated example, the system is implemented on a single server 500. However, the functions of the system may be implemented across distributed devices 500, 502, 504, etc. connected to one another through a communication link. In other examples, functionality of the system may be distributed across any number of devices, including the portable personal computer, smart phone, electronic document, tablet, and desktop personal computer devices shown. In other examples, the functions of the system may be cloud based, such as, for example one or more connected cloud TPU (s) customized to perform machine learning processes. The network 1250 may be a public network such as the Internet, private network such as a research institution's or corporation's private network, or any combination thereof. Networks can include, local area network (LAN), wide area network (WAN), cellular, satellite, or other network infrastructure, whether wireless or wired. The network can utilize communications protocols, including packet-based and/or datagram-based protocols such as internet protocol (IP), transmission control protocol (TCP), user datagram protocol (UDP), or other types of protocols. Moreover, the network can include a number of devices that facilitate network communications and/or form a hardware basis for the networks, such as switches, routers, gateways, access points (such as a wireless access point as shown), firewalls, base stations, repeaters, backbone devices, etc.

The computer-readable media 1212 may include executable computer-readable code stored thereon for programming a computer (e.g., comprising a processor(s) and GPU(s)) to the techniques herein. Examples of such computer-readable storage media include a hard disk, a CD-ROM, digital versatile disks (DVDs), an optical storage device, a magnetic storage device, a ROM (Read Only Memory), a PROM (Programmable Read Only Memory), an EPROM (Erasable Programmable Read Only Memory), an EEPROM (Electrically Erasable Programmable Read Only Memory) and a Flash memory. More generally, the processing units of the computing device 1300 may represent a CPU-type processing unit, a GPU-type processing unit, a TPU-type processing unit, a field-programmable gate array (FPGA), another class of digital signal processor (DSP), or other hardware logic components that can be driven by a CPU.

Exemplary Computer-Implemented Methods

Figure 6:
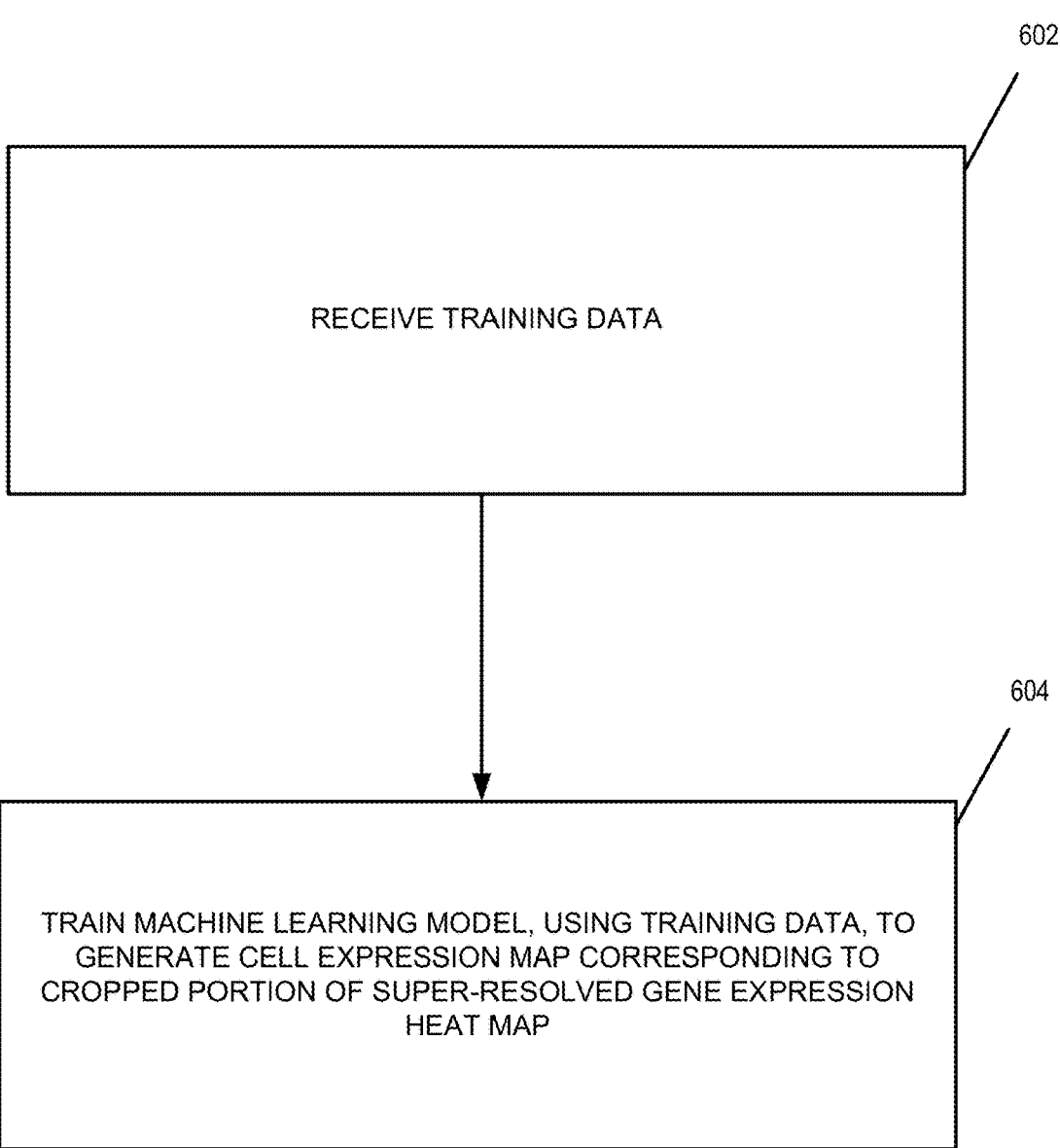
FIG. 6 depicts an exemplary method, according to some aspects.

FIG. 6 depicts an exemplary method 600 for training a machine learning model to classify cells in a histology image, according to some aspects.

The method 600 may include receiving, via one or more processors, training data (block 602). The method 600 may include training a machine learning model, using the training data, to generate a cell expression map corresponding to a cropped portion of a super-resolved gene expression heat map, wherein the cell expression map includes a plurality of cell contours, each including respective aggregated gene expression values (block 604). Specifically, the plurality of cell contours to segment cells allow the accurate registration of transcriptomic data. In some aspects, the training data includes at least one of (i) one or more cell segmentation maps, (ii) one or more spatial transcriptomics data sets, and (iii) one or more pathologists' annotations. In some aspects, at least one of the cell segmentation maps corresponds to a respective one of the spatial transcriptomics data sets and to a respective one of the pathologists' annotations.

In some aspects, the method 600 may include training the machine learning model on one or more genes to infer genes expressed for a given cell contour. In some aspects, the method 600 may include training the machine learning model infer human spatial cell types and gene expression from animal model system tissues. For example, the method 600 may train the machine learning model on an histology image of paired animal model system tissues such as mouse and corresponding human tissue and/or a cell segmentation map.

In some aspects, the method 600 further includes training a machine learning model to generate histology images corresponding to an antecedent time point or a subsequent time point. The method 600 may train such a model using gene expression images from animal model systems or human samples.

In some aspects, the method 600 may include gene inference of histology images and cell segmentation beyond the confines of a histology region that is captured by the spatial transcriptomics chemistry, to identify cell types and expressed gene(s). For example, for a structured image, where an epithelial layer abuts the edge of a Visium capture area.

In some aspects, the method 600 further includes generating an image mask corresponding to the training data; and providing the image mask to the machine learning model with the training data, to enable the model to output features enabling model outputs to be matched to model inputs.

In some aspects, the method 600 further includes training the machine learning model to determine the cropped portion of the super-resolved gene expression heat map by linking coordinates of the super-resolved gene expression heat map to coordinates of images in the training data.

FIG. 7 depicts an exemplary method 700 for classifying cells in an histology image, according to some aspects. The method 700 may include receiving, via one or more processors, the histology image and a cell segmentation map (block 702). The method 700 may include processing the histology image and the cell segmentation map using a trained machine learning model to generate a cell expression map including a plurality of cell contours, each including a respective predicted aggregated gene expression, wherein the machine learning model is trained using training data; and for each of the cell contours, processing the cell contour to generate a respective predicted cell type using a model trained to predict cell types based on aggregated gene expression information (block 704).

In some aspects, the aggregated gene expression information includes an abundance value or expression level for each gene in a plurality of genes.

In some aspects, processing the cell contour to generate the respective cell type includes generating a gene-by-gene comatrix, wherein one dimension of the comatrix represents one individual cell and another dimension represents an expression value for a particular gene for a particular cell.

In some aspects, the method 700 may further include processing each cell contour's gene expression profile using a trained cell type prediction machine learning model to determine a type of the cell.

In some aspects, the trained cell type prediction machine learning model is a logistic regression machine learning model.

The method 600 and/or the method 700 may be implemented by the computing device 500 of FIG. 500 and the other elements of FIG. 5, in some aspects.

ADDITIONAL CONSIDERATIONS

It should be understood that the examples given above are illustrative and do not limit the uses of the systems and methods described herein in combination with a digital and laboratory health care platform.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components or multiple components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a microcontroller, field programmable gate array (FPGA) or an application-specific integrated circuit (ASIC)) to perform certain operations. A hardware module may also comprise programmable logic or circuitry (e.g., as encompassed within a processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a processor configured using software, the processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connects the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of the example methods described herein can be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method can be performed by one or more processors or processor-implemented hardware modules. The performance of certain of the operations may be distributed among the one or more processors, not only residing within a single machine, but also deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but also deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

This detailed description is to be construed as an example only and does not describe every possible embodiment, as describing every possible embodiment would be impractical, if not impossible. One could implement numerous alternative embodiments, using either current technology or technology developed after the filing date of this application.

What is claimed is:

1. A computer-implemented method for training a machine learning model to classify cells in a histology image, the method comprising:
receiving, via one or more processors, training data; and
training a machine learning model, using the training data, to generate a cell expression map corresponding to a cropped portion of a super-resolved gene expression heat map,
wherein the cell expression map includes a plurality of cell contours, each including respective aggregated gene expression values.

2. The computer-implemented method of claim 1, wherein the training data includes at least one of (i) one or more cell segmentation maps, (ii) one or more spatial transcriptomics data sets, and (iii) one or more pathologists' annotations.

3. The computer-implemented method of claim 2, wherein at least one of the cell segmentation maps corresponds to a respective one of the spatial transcriptomics data sets and to a respective one of the pathologists' annotations.

4. The computer-implemented method of claim 1, further comprising:
generating an image mask corresponding to the training data; and providing the image mask to the machine learning model with the training data, to enable the model to output features enabling model outputs to be matched to model inputs.

5. The computer-implemented method of claim 1, further comprising:

training the machine learning model to determine the cropped portion of the super-resolved gene expression heat map by linking coordinates of the super-resolved gene expression heat map to coordinates of images in the training data.

6. A computer-implemented method for classifying cells in an histology image, the method comprising:

receiving, via one or more processors, the histology image and a cell segmentation map;

processing the histology image and the cell segmentation map using a trained machine learning model to generate a cell expression map including a plurality of cell contours, each including a respective predicted aggregated gene expression, wherein the machine learning model is trained using training data; and for each of the cell contours, processing the cell contour to generate a respective predicted cell type using a model trained to predict cell types based on aggregated gene expression information.

7. The computer-implemented method of claim 6, wherein the aggregated gene expression information includes an abundance value or expression level for each gene in a plurality of genes.

8. The computer-implemented method of claim 6, wherein processing the cell contour to generate the respective cell type includes generating a gene-by-gene comatrix, wherein one dimension of the comatrix represents one individual cell and another dimension represents an expression value for a particular gene for a particular cell.

9. The computer-implemented method of claim 6, further comprising:

processing each cell contour's gene expression profile using a trained cell type prediction machine learning model to determine a type of the cell.

10. The computer-implemented method of claim 9, wherein the trained cell type prediction machine learning model is a logistic regression machine learning model.

11. A computing system for training a machine learning model to classify cells in a histology image, comprising:

one or more processors; and one or more memories having stored thereon computer-executable instructions that, when executed by the one or more processors, cause the computing system to:

receive, via one or more processors, training data; and train a machine learning model, using the training data, to generate a cell expression map corresponding to a cropped portion of a super-resolved gene expression heat map, wherein the cell expression map includes a plurality of cell contours, each including respective aggregated gene expression values.

12. The computing system of claim 11, wherein the training data includes at least one of (i) one or more cell segmentation maps, (ii) one or more spatial transcriptomics data sets, and (iii) one or more pathologists' annotations.

13. The computing system of claim 12, wherein at least one of the cell segmentation maps corresponds to a respective one of the spatial transcriptomics data sets and to a respective one of the pathologists' annotations.

14. The computing system of claim 11, the instructions having stored thereon further instructions that, when executed by the one or more processors, cause the computing system to:

generate an image mask corresponding to the training data; and provide the image mask to the machine learning model with the training data, to enable the model to output features enabling the model output to be matched to model inputs.

15. The computing system of claim 11, the instructions having stored thereon further instructions that, when executed by the one or more processors, cause the computing system to:

train the machine learning model to determine the cropped portion of the super-resolved gene expression heat map by linking coordinates of the super-resolved gene expression map to coordinates of images in the training data.

16. A computing system for training a machine learning model to classify cells in a histology image, comprising:

one or more processors; and one or more memories having stored thereon computer-executable instructions that, when executed by the one or more processors, cause the computing system to:

receive, via one or more processors, the histology image and a cell segmentation map;

process the histology image and the cell segmentation map using a trained machine learning model to generate a cell expression map including a plurality of cell contours, each including a respective predicted aggregated gene expression, wherein the machine learning model is trained using training data; and for each of the cell contours, process the cell contour to generate a respective predicted cell type using a model trained to predict cell types based on aggregated gene expression information.

17. The computing system of claim 16, wherein the aggregated gene expression information includes an abundance value or expression level for each gene in a plurality of genes.

18. The computing system of claim 16, the instructions having stored thereon further instructions that, when executed by the one or more processors, cause the computing system to:

generate a gene-by-gene comatrix, wherein one dimension of the comatrix represents one individual cell and another dimension represents an expression value for a particular gene for a particular cell.

19. The computing system of claim 16, the instructions having stored thereon further instructions that, when executed by the one or more processors, cause the computing system to:

process each cell contour's gene expression profile using a trained cell type prediction machine learning model to determine a type of the cell.

20. The computing system of claim 19, wherein the trained cell type prediction machine learning model is a logistic regression machine learning model.

21. A non-transitory computer-readable medium having stored thereon computer-executable instructions that, when executed by one or more processors, cause a computer to:

receive, via one or more processors, training data; and train a machine learning model, using the training data, to generate a cell expression map corresponding to a cropped portion of a super-resolved gene expression heat map, wherein the cell expression map includes a plurality of cell contours, each including respective aggregated gene expression values.

22. A non-transitory computer-readable medium having stored thereon computer-executable instructions that, when executed by one or more processors, cause a computer to:

receive, via one or more processors, a histology image and a cell segmentation map;

process the histology image and the cell segmentation map using a trained machine learning model to generate a cell expression map including a plurality of cell contours, each including a respective predicted aggregated gene expression, wherein the machine learning model is trained using training data; and for each of the cell contours, process the cell contour to generate a respective predicted cell type using a model trained to predict cell types based on aggregated gene expression information.

* * * * *